(12) United States Patent
Whitman et al.

(10) Patent No.: US 8,764,795 B2
(45) Date of Patent: Jul. 1, 2014

(54) TISSUE CLOSURE DEVICE AND METHOD

(75) Inventors: Michael P. Whitman, New Hope, PA (US); Peter Datcuk, Quakertown, PA (US)

(73) Assignee: Micro Interventional Devices, Inc., New Hope, PA (US)

(*) Notice: Subject to any disclaimer, the term of this patent is extended or adjusted under 35 U.S.C. 154(b) by 626 days.

(21) Appl. No.: 13/010,769

(22) Filed: Jan. 20, 2011

(65) Prior Publication Data

US 2012/0022586 A1 Jan. 26, 2012

Related U.S. Application Data

(60) Provisional application No. 61/296,868, filed on Jan. 20, 2010.

(51) Int. Cl.
*A61B 17/08* (2006.01)

(52) U.S. Cl.
USPC .......................................................... 606/216

(58) Field of Classification Search
USPC ......... 606/213, 215, 216, 219, 142, 153, 151; 227/175.1; 623/23.72
See application file for complete search history.

(56) References Cited

U.S. PATENT DOCUMENTS

| | | | |
|---|---|---|---|
| 3,959,960 A | 6/1976 | Santos | |
| 4,204,541 A | 5/1980 | Kapitanov | |
| 4,488,523 A | 12/1984 | Shichman | |
| 4,669,473 A | 6/1987 | Richards et al. | |
| 4,741,330 A | 5/1988 | Hayhurst | |
| 4,873,976 A | 10/1989 | Schreiber | |
| 4,884,572 A | 12/1989 | Bays et al. | |
| 5,356,424 A | 10/1994 | Buzerak et al. | |
| 5,370,661 A | 12/1994 | Branch | |
| 5,562,704 A | 10/1996 | Tamminmaki et al. | |
| 5,584,859 A * | 12/1996 | Brotz ............................ | 606/228 |
| 5,782,844 A | 7/1998 | Yoon et al. | |
| 5,964,782 A * | 10/1999 | Lafontaine et al. ........... | 606/213 |
| 5,993,475 A | 11/1999 | Lin et al. | |
| 6,387,113 B1 | 5/2002 | Hawkins et al. | |
| 6,663,633 B1 | 12/2003 | Pierson, III | |
| 6,692,499 B2 * | 2/2004 | Tormala et al. ............... | 606/213 |
| 7,037,315 B2 | 5/2006 | Sancoff et al. | |
| 7,104,949 B2 | 9/2006 | Anderson et al. | |
| 7,220,265 B2 | 5/2007 | Chanduszko et al. | |
| 7,361,185 B2 * | 4/2008 | O'Malley et al. ............. | 606/215 |
| 7,833,238 B2 * | 11/2010 | Nakao ............................ | 606/151 |
| 2003/0074021 A1 | 4/2003 | Morriss et al. | |
| 2003/0092969 A1 | 5/2003 | O'Malley et al. | |
| 2003/0097148 A1 | 5/2003 | Valimaa et al. | |

(Continued)

FOREIGN PATENT DOCUMENTS

WO 2007/098212 A2 8/2007

*Primary Examiner* — Melanie Tyson
*Assistant Examiner* — Katelyn Bernier
(74) *Attorney, Agent, or Firm* — Kenyon & Kenyon LLP

(57) ABSTRACT

A device having a plurality of anchors configured to be driven into a tissue, and a closure element extending between the anchors and configured to urge the anchors from a first configuration in which the anchors are a first distance from each other, toward a second configuration in which the anchors are a second distance from each other, the second distance being less than the first distance, wherein the device is configured to maintain the anchors in the first configuration during a surgical intervention and to subsequently allow the anchors to be moved by the closure element toward the second configuration.

34 Claims, 35 Drawing Sheets

(56) References Cited

U.S. PATENT DOCUMENTS

| | | | |
|---|---|---|---|
| 2004/0087981 A1 | 5/2004 | Berube et al. | |
| 2004/0220596 A1 | 11/2004 | Frazier et al. | |
| 2004/0220610 A1 | 11/2004 | Kreidler et al. | |
| 2005/0021057 A1 | 1/2005 | St. Goar et al. | |
| 2005/0187568 A1 | 8/2005 | Klenk et al. | |
| 2005/0234508 A1* | 10/2005 | Cummins et al. | 606/213 |
| 2005/0251175 A1* | 11/2005 | Weisenburgh et al. | 606/153 |
| 2005/0256532 A1 | 11/2005 | Nayak et al. | |
| 2006/0004364 A1 | 1/2006 | Green et al. | |
| 2006/0030884 A1 | 2/2006 | Yeung et al. | |
| 2006/0282088 A1 | 12/2006 | Ryan | |
| 2006/0287661 A1 | 12/2006 | Bolduc | |
| 2007/0112425 A1* | 5/2007 | Schaller et al. | 623/2.37 |
| 2007/0142837 A1 | 6/2007 | Dreyfuss | |
| 2007/0185530 A1* | 8/2007 | Chin-Chen et al. | 606/213 |
| 2007/0203511 A1 | 8/2007 | Vardi | |
| 2008/0132948 A1* | 6/2008 | Surti et al. | 606/232 |
| 2008/0161850 A1 | 7/2008 | Weisenburgh et al. | |
| 2008/0228193 A1 | 9/2008 | Matityahu et al. | |
| 2009/0024163 A1 | 1/2009 | Zeiner et al. | |
| 2009/0198107 A1 | 8/2009 | Park et al. | |
| 2009/0216264 A1 | 8/2009 | Friedman et al. | |
| 2009/0228040 A1* | 9/2009 | Mas et al. | 606/216 |
| 2009/0236401 A1 | 9/2009 | Cole et al. | |
| 2009/0240264 A1 | 9/2009 | Tuval et al. | |
| 2009/0248067 A1 | 10/2009 | Maiorino | |
| 2009/0275960 A1 | 11/2009 | Provenza et al. | |
| 2009/0287304 A1* | 11/2009 | Dahlgren et al. | 623/2.37 |
| 2010/0010457 A1 | 1/2010 | Ewers et al. | |
| 2010/0087854 A1 | 4/2010 | Stopek et al. | |
| 2011/0028995 A1 | 2/2011 | Miraki et al. | |
| 2012/0059395 A1 | 3/2012 | Kehdy et al. | |
| 2012/0116418 A1 | 5/2012 | Belson | |

* cited by examiner

TISSUE CLOSURE DEVICE AND METHOD

CROSS-REFERENCE TO RELATED APPLICATIONS

This application claims the benefit of U.S. Provisional Patent Application Ser. No. 61/296,868, filed on Jan. 20, 2010, which is hereby incorporated herein in its entirety by reference thereto.

Further, each of the following is hereby incorporated in its entirety by reference thereto: U.S. patent application Ser. No. 13/010,766, filed on Jan. 20, 2011, U.S. patent application Ser. No. 13/010,777, filed on Jan. 20, 2011; and U.S. patent application Ser. No. 13/010,774, filed on Jan. 20, 2011.

FIELD OF THE INVENTION

The present invention relates to a tissue closure device and method.

BACKGROUND INFORMATION

Some surgical interventions involve piercing or cutting a hole into a tissue wall. For example, thoracoscopic procedures typically involve piercing one or more tissue walls with a trocar or other sharp device and insertion of a cannula to maintain an opening in the tissue. Surgical instruments may be inserted through the cannula in order to access a surgical site disposed beyond the tissue. For example, a thoracoscopic cardiac procedure may involve a trans-apical valve repair. This procedure requires access to the outer wall of patient's heart, e.g., via a small intercostal hole in the patient. This procedure further involves piercing the outer wall of the heart to form an access hole, and insertion of a cannula to maintain a desired diameter of the access hole and to protect the pierced heart tissue during subsequent insertion and/or removal of thoracoscopic tools through the cannula. Thoracoscopic surgical tools may then be inserted through the cannula and into one or more chambers of the heart in order to repair defects or damaged portions of the heart.

Further, some pericardiocentesis procedures involve inserting a needle, via an intercostal opening in the patient, into the pericardial sac, guiding a flexible guide wire through the needle, and subsequent removal of the needle with the guide wire left in place. After removal of the needle, a tapered dilator may be advanced over the guide wire to dilate the opening in the pericardium tissue. The dilated opening, or tract, allows room for a catheter. After the dilation, the catheter is guided over the guide wire into the pericardial sac to drain fluid from the pericardium.

Thoracoscopic surgical procedures are generally less intrusive than more traditional forms of surgery, since they generally require relatively small entry openings. However, these small openings may be difficult to close, especially where the closure location is inside the patient's body. For example, referring the procedures described above, after removal of the cannula and any surgical instruments extending therethrough, the aperture formed in the tissue, e.g., the heart or pericardium tissue, is closed within the patient's body. Since these exemplary thoracoscopic procedures involve accessing the *patient's thorax through a small intercostal aperture through the patient's skin and other underlying tissues (e.g., fat and/or fascia), closure methods such as suturing are more complicated than with non-thoracoscopic surgical procedures. In particular, applying sutures with remotely operated thoracoscopic instruments is more difficult and complicated than directly manipulating a suture needle by hand at the surgical site. This difficulty can result in defective closures and/or closures that require more time than necessary.

Defective closures may expose the patient to increased risk of complications such as internal bleeding and/or infection. Even where defective closures are recognized and addressed prior to completion of the surgical procedure, the correction of defective closures increases the time required to effect the closure and may expose the tissue to additional trauma. It is generally desirable to minimize the amount of time for a surgical procedure in order to reduce the possibility of complications and unnecessary trauma to the patient.

Thus, there is a need for a closure mechanism and method that is simple to operate, reliable, and requires a small amount of time in which to form an effective closure.

SUMMARY

In accordance with example embodiments of the present invention, a device includes: a plurality of anchors; at least one elastic closure element coupled to the anchors and configured to urge the anchors toward each other; and a driver configured to drive the anchors, with the closure element coupled to the anchors, into tissue; wherein the closure element has an elasticity sufficient to urge the anchors, driven into the tissue, toward each other to close an aperture in the tissue located between the anchors driven into the tissue and to resist opposing forces exerted on the anchors that urge the anchors apart.

The opposing forces may be exerted on the anchors by at least one of (a) the tissue, (b) a fluid flow, (c) pneumatic pressure, (d) hydraulic pressure, and (e) external forces.

The device may further include a safety release mechanism including a plurality of spring-loaded members, each spring-loaded member independently movable between an engagement position and a disengagement position, the safety release mechanism adapted to prevent the driver from driving the anchors unless all of the spring-loaded members are in the engagement position.

The anchors may each include an elongated body having a distal tip configured to pierce the tissue when the respective anchor is distally driven into the tissue.

The anchors may each include an anchoring projection configured to resist proximal movement of the anchor after the anchor is driven into the tissue.

The anchoring projection is a wing extending proximally and radially from a connection between the wing and the elongated body to a free end.

The wing may include a plurality of proximally extending cutting projections at the free end of the wing.

The wing may be formed by a cut progressing radially inwardly and distally into the elongated body.

The elongated body and the wing may include a plurality of longitudinally extending corrugations, the corrugations providing a plurality of proximally extending cutting projections at the free end of the wing.

The anchors may each include first and second anchoring projections configured to resist proximal movement of the anchor after the anchor is driven into the tissue, the first and second anchoring projections being disposed at respective positions that are offset from each other along the length of the elongated body.

The first and second anchoring projections may be first and second wings formed respectively by first and second cuts progressing radially inwardly and distally into the elongated body and ending at respective locations that are offset from each other along the length of the elongated body.

The closure element may include at least one of a band, an elastomeric band, and a band formed of silicon.

The anchors may each include a hooked projection configured to receive the band.

The hooked projection may be configured to maintain engagement between the band and the anchor by preventing the band from moving off the proximal end of the anchor.

The device may include a plurality of closure elements.

Each of the plurality of closure elements may contact two or more of the anchors.

The closure elements may form a pattern of two overlapping V-shaped configurations.

The plurality of closure elements may contact three or more of the anchors.

The at least one closure element may include a monolithic V-shaped element coupling three of the anchors.

The device may include two monolithic V-shaped closure elements each configured to contact three of the anchors. The two V-shaped closure elements may overlap to form a diamond-shaped operational window.

The device may further include a centering element configured to receive a guide wire. The centering element may be a tubular shaft.

The anchors may be disposed along a ring-shaped circumference in the first configuration.

The closure element may be prevented from extending within the ring-shaped circumference by one or more tubes.

The driver may configured to simultaneously drive the plurality of anchors.

The driver may comprise a spring-loaded element configured to impact and impart a distally directed momentum to the anchors.

The device may further include a trigger configured to release the spring-loaded element from a preloaded position in order to drive the plurality of anchors.

The device may further include a handle, the trigger being disposed in handle.

The handle, the trigger, and the driver may be detachable from the cannula, the outer working tube, the plurality of anchors, and the closure element.

The plurality of anchors and the closure element may be formed of bioabsorbable materials.

In accordance with example embodiments of the present invention, a device includes: a plurality of anchors; and at least one elastic closure element coupled to the anchors and configured to urge the anchors toward each other; wherein the closure element has an elasticity sufficient to urge the anchors, driven into the tissue, toward each other to close an aperture in the tissue located between the anchors driven into the tissue and to resist opposing forces exerted on the anchors that urge the anchors apart.

The opposing forces may be exerted on the anchors by at least one of (a) the tissue, (b) a fluid flow, (c) pneumatic pressure, (d) hydraulic pressure, and (e) external forces.

In accordance with example embodiments of the present invention, a method includes: implanting a plurality of anchors into tissue; and urging the implanted anchors towards each other by at least one elastic closure element coupled to the anchors with sufficient force to (a) close an aperture in the tissue located between the implanted anchors and (b) resist opposing forces exerted on the implanted anchors that urge the anchors apart and the aperture open.

The opposing forces may be exerted on the anchors by at least one of (a) the tissue, (b) a fluid flow, (c) pneumatic pressure, (d) hydraulic pressure, and (e) external forces.

In accordance with example embodiments of the present invention, a method includes: implanting a plurality of anchors into tissue; urging the implanted anchors towards each other by at least one elastic closure element coupled to the anchors; forming an aperture in the tissue between the implanted anchors, the elastic closure element urging the implanted anchors towards each other and towards the aperture with sufficient force to (a) maintain the aperture in the tissue in a closed position and (b) resist opposing forces exerted on the implanted anchors that urge the anchors apart and urges the aperture open; inserting an instrument through the aperture; and after removing the instrument from the aperture, again urging the implanted anchors towards each other and towards the aperture by the elastic closure element with sufficient force to (a) maintain the aperture in the tissue in the closed position and (b) resist opposing forces exerted on the implanted anchors that urge the anchors apart and the aperture open.

The opposing forces may be exerted on the anchors by at least one of (a) the tissue, (b) a fluid flow, (c) pneumatic pressure, (d) hydraulic pressure, and (e) external forces.

In accordance with example embodiments of the present invention, a method includes: forming an aperture in tissue; inserting a centering device through the aperture; implanting a plurality of anchors into the tissue using the centering device to center the anchors about the aperture; urging the implanted anchors towards each other and towards the aperture by at least one elastic closure element coupled to the anchors; inserting an instrument through the aperture; and after removing the instrument from the aperture, again urging the implanted anchors towards each other and towards the aperture by the elastic closure element with sufficient force to (a) maintain the aperture in the tissue in the closed position and (b) resist opposing forces exerted on the implanted anchors that urge the anchors apart and the aperture open.

The opposing forces may be exerted on the anchors by at least one of (a) the tissue, (b) a fluid flow, (c) pneumatic pressure, (d) hydraulic pressure, and (e) external forces.

In accordance with example embodiments of the present invention, a surgical device comprises two or more anchors, a driver configured to drive the anchors into a tissue, and at least one elastic closure element extending between the anchors and configured to urge the anchors from a first configuration in which the anchors are a first distance from each other, toward a second configuration in which the anchors are a second distance from each other, the second distance being less than the first distance, wherein the surgical device is configured to maintain the driven anchors in the first configuration and to selectably release the driven anchors to allow the anchors to be moved by the at least one closure element toward the second configuration.

The anchors may each include an elongated body having a distal tip configured to pierce the tissue when the respective anchor is distally driven into the tissue.

The anchors may each include an anchoring projection configured to resist proximal movement of the anchor after the anchor is driven into the tissue.

The anchoring projection may be a wing extending proximally and radially from a connection between the wing and the elongated body to a free end.

The wing may include a plurality of proximally extending cutting projections at the free end of the wing.

The wing may be formed by a cut progressing radially inwardly and distally into the elongated body.

The elongated body and the wing may include a plurality of longitudinally extending corrugations, the corrugations providing a plurality of proximally extending cutting projections at the free end of the wing.

The anchors may each include first and second anchoring projections configured to resist proximal movement of the anchor after the anchor is driven into the tissue, the first and second anchoring projections being disposed at respective positions that are offset from each other along the length of the elongated body.

The first and second anchoring projections may be first and second wings formed respectively by first and second cuts progressing radially inwardly and distally into the elongated body and ending at respective locations that are offset from each other along the length of the elongated body.

The closure element may be a band. The band may form a continuous loop. The band may be elastomeric. The band may be formed of silicon.

The anchors may each include a hooked projection configured to receive the band.

The hooked projection may be configured to maintain engagement between the band and the anchor by preventing the band from moving off the proximal end of the anchor.

The device may include a two or more closure elements. Each of the plurality of closure elements may contact only two of the anchors. For example, the two or more closure elements may include four closure elements or may include six anchors, two of the six anchors being connected to only two of four closure elements, and four of the six anchors being connected to only a respective one of the four closure elements. The closure elements may form a pattern of two or more overlapping V-shaped configurations.

The surgical plurality of closure elements may contact three or more of the anchors.

The at least one closure element may include a monolithic V-shaped element configured to contact three of the anchors.

The at least one closure element may include two or more monolithic V-shaped elements each configured to contact three of the anchors. For example, the V-shaped elements may overlap to form a diamond-shaped operational window.

The device may further comprise a centering element configured to receive a guide wire. The device of claim 25, wherein the centering element is a tubular shaft. The centering element may have a proximal portion configured to allow the centering mechanism to be retracted from the remainder of the surgical device.

The device may further comprise at least one pressure sensor configured to indicate whether the device is adequately contacting the tissue prior to driving the anchors.

The at least one pressure sensor may include at least one contact element extending distally from a distal end of the device. The at least one contact element may be depressible when a distal end of the device is pressed against the tissue.

The device may further comprise a key plate and at least one key member, the at least one key member having a first position in which the at least key member is engaged with the key plate and a second position in which the at least one key member is disengaged with the key plate, wherein depression of the contact element causes the at least one key member to move from the first position to the second position.

The key plate may prevent driving of the anchors when the at least one key member is engaged with the key plate.

The at least one key member includes a plurality of key members each being independently movable by a respective contact element. The key plate may prevent driving of the anchors if any one of the key members is engaged with the key plate.

The anchors may be disposed along a ring-shaped circumference in the first configuration.

The closure element may be prevented from extending within the ring-shaped circumference when the anchors are maintained in the first configuration.

The surgical device may further comprise a cannula configured to provide access to a surgical site disposed between the anchors when the anchors are maintained in the first configuration.

The cannula may be configured to maintain the anchors in the first configuration.

The anchors and closure element may be disposed at a position radially exterior to the cannula.

The surgical device may further comprise an outer working tube, the cannula extending within the outer working tube.

At least one of the cannula and the outer working tube may have an outer surface configured to prevent the anchor and the closure element from extending to any radial position corresponding to an interior of the cannula.

The surgical device may include a plurality of closure elements prevented from extending to any radial position corresponding to the interior channel of the cannula.

The cannula may include a distal portion having a flanged orientation in which the distal portion forms a radially extending flange configured to prevent the closure elements from moving distally beyond the distal end of the cannula. The flange may extend radially beyond an outer surface of the outer working tube.

The distal portion of the cannula may be actuatable to a second orientation, in which the distal portion of the inner working channel does not prevent the closure elements from moving distally beyond the distal end of the cannula.

The flange may extend distally when the distal portion of the cannula is in the second orientation.

The distal portion of the cannula may be actuatable from the flanged orientation to the second orientation by proximally sliding the cannula with respect to the outer working tube.

The depth to which the anchors are driven by the driver may be limited by contact between the closure element and the radially extending flanges.

The driver may be configured to simultaneously drive the plurality of anchors.

The driver may comprise a spring-loaded element configured to impact and impart a distally directed momentum to the anchors.

The surgical device may further comprise a trigger configured to release the spring-loaded element from a preloaded position in order to drive the plurality of anchors.

The surgical device may further comprise a handle, the trigger being disposed in handle.

The surgical device may further comprise a safety element configured to prevent the trigger from releasing the spring-loaded element when the safety element is in a safety position.

The handle, the trigger, and the driver may be detachable from the cannula, the outer working tube, the plurality of anchors, and the closure element.

The plurality of anchors and/or the closure element may be formed of bioabsorbable materials.

In accordance with example embodiments of the present invention, a method comprises: implanting two or more anchors into a tissue; maintaining the implanted anchors in a first configuration in which the anchors are a first distance from each other; urging the anchors from the first configuration toward a second configuration in which the anchors are a second distance from each other, the second distance being less than the first distance; forming an aperture in the tissue in an area between the two or more anchors; and constricting the aperture by allowing the anchors to move from the first configuration to the second configuration.

The aperture may be formed while the implanted anchors are maintained in the first configuration.

The aperture may be formed with a trocar.

The method may further comprise performing a thoracoscopic surgical procedure through the aperture.

The closure device may include a cannula configured to maintain the closure device in the preloaded state, the thoracoscopic surgical procedure being performed through the cannula.

The tissue may be a heart tissue.

The thoracoscopic surgical procedure may be a trans-apical valve repair.

In accordance with example embodiments of the present invention, a surgical device comprises a plurality of anchors configured to be driven into a tissue, and at least one closure element extending between the anchors and configured to urge the anchors from a first configuration in which the anchors are a first distance from each other, toward a second configuration in which the anchors are a second distance from each other, the second distance being less than the first distance, wherein the surgical device is configured to maintain the anchors in the first configuration during a surgical procedure and to subsequently allow the anchors to be moved by the closure element toward the second configuration.

In accordance with example embodiments of the present invention, a surgical device comprises a driver configured to drive a plurality of anchors into a tissue in a first anchor configuration in which the anchors are a first distance from each other, wherein the device is configured to maintain the driven anchors in the first anchor configuration and to selectably release the driven anchors to allow the anchors to be moved by at least one closure element toward a second anchor configuration in which the anchors are closer to each other than when the anchors are in the first anchor configuration.

The driver may be configured to drive each anchor by striking, e.g., a) the respective anchor or b) a pin configured to transfer momentum from the driver to the anchor.

The driver may be configured to be actuated from a proximal position to a distal position in which the driver imparts momentum to each respective anchor by striking a) the respective anchor or b) a pin configured to transfer momentum from the driver to the respective anchor. The driver may be configured to be actuated by a spring.

Further features and aspects of example embodiments of the present invention are described in more detail below with reference to the appended Figures.

DETAILED DESCRIPTION

Figure 1:
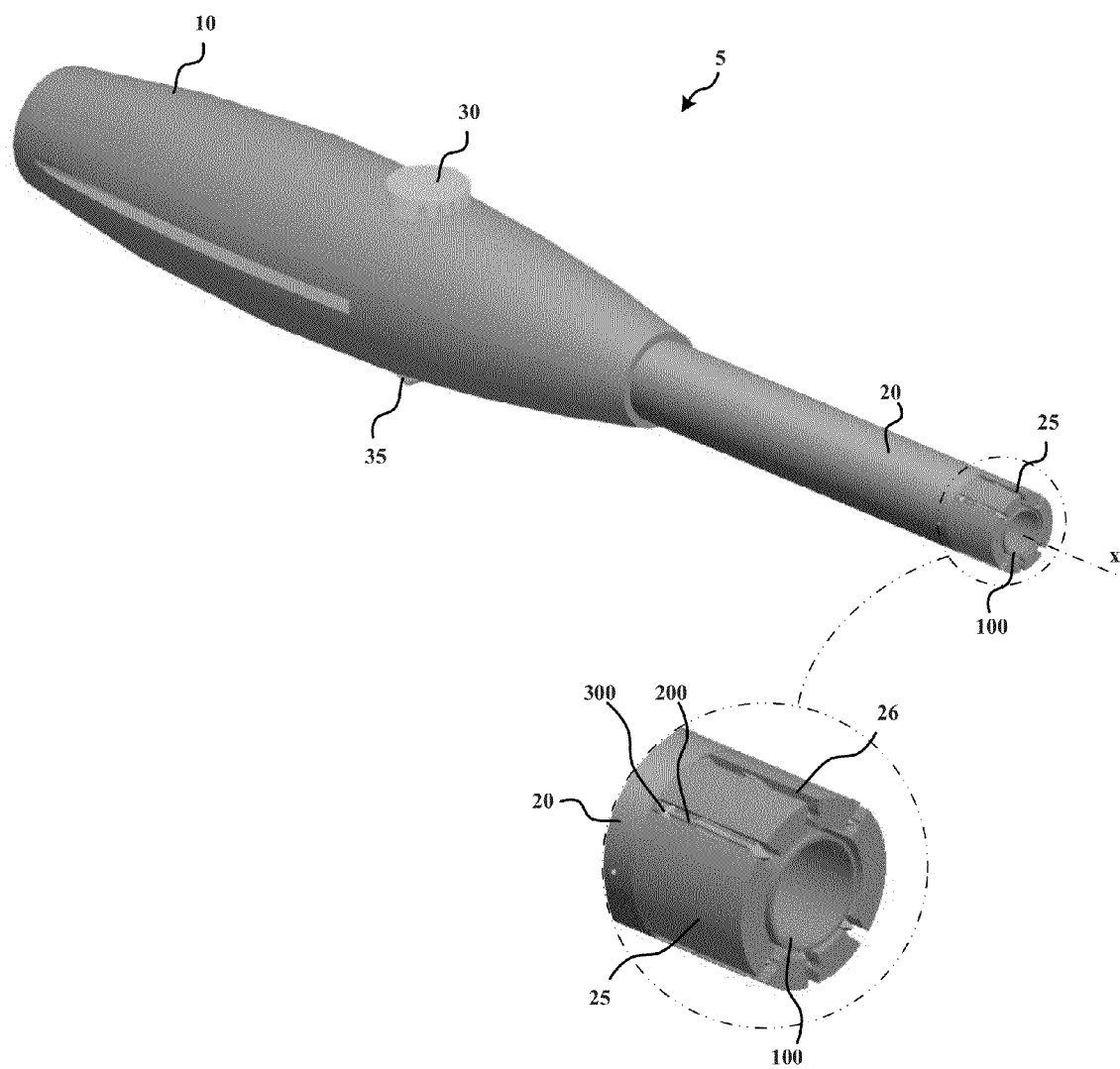
FIGS. 1 and 2 show a surgical closure device and a detailed view of a distal tip of the surgical device in accordance with an example embodiment of the present invention.

As set forth in greater detail below, example embodiments of the present invention allow for the reliable and effective closure of an opening in tissue (e.g., a pericardial window) that limits the possibility of human error, e.g., by eliminating the need for suturing. In some examples, a surgical device anchors a plurality of anchors, which are connected to each other by one or more elastic closure elements, into the tissue. The anchors are driven into the tissue in a spaced-apart configuration in which the elastic closure elements are tensioned between the anchors. The anchors are held in the spaced-apart arrangement while a surgical procedure is performed through a tissue opening formed between the anchored locations of the anchors. In order to close the opening, the device simply releases the anchors from the spaced-apart arrangement such that the tensioned elastic closure elements draw the anchors, as well as the tissue in which the anchors are anchored, toward the tissue opening. Thereby, the tissue opening is held closed. The tension remaining in the elastic closure elements offsets the opposing forces that may be entered on the anchors by at least one of (a) the tissue, (b) the fluid flow, (c) pneumatic pressure, (d) hydraulic pressure, and (e) external forces.

Referring, for example, to FIGS. 1 to 10E, a surgical procedure involves positioning a surgical closure device 5 at a surgical entry location, e.g., a location on the wall of a heart where access to the interior of the heart is desired. The surgical closure device 5 is then actuated, e.g., via a trigger, to drive a plurality of anchors 200 into the tissue at predetermined locations spaced around the surgical entry location. The anchors 200 are preloaded toward the entry location by pre-tensioned closure elements 300 in the form of elastic bands. The anchors 200 are maintained in their outward positions by a cannula 400 and/or an outer working tube 100. After the anchors 200 are driven, the portions of the surgical device other than the cannula 400, outer working tubes 100, the anchors 200, and the closure elements 300 are removed.

The cannula 400 then provides a working channel through which the surgical procedure may be performed. For example, a trocar may be extended through the channel of the cannula 400 to pierce the tissue 900. Other surgical instruments may then be inserted through the working channel in accordance with any suitable thoracoscopic procedure. To conclude the procedure, any thoracoscopic surgical tools extending through the working channel are withdrawn and the cannula 400 and working tube 100 are proximally withdrawn from the surgical entry location. The withdrawal of the cannula 400 and working tube 100 causes the pre-tensioned closure elements 300 to draw the anchors 200 toward the surgical entry site. Since the anchors 200 are anchored in the tissue surrounding the surgical entry location, this results in the tissue surrounding the surgical entry location being drawn together, thereby closing the surgical entry hole. In contrast to conventional procedures, no sutures are required.

Although a cannula 400 is provided separately from the outer working tube 100, it should be understood that example embodiments may include only a single tube. For example, if the cannula 400 is not provided in the device 5, the working tube 100 functions as the cannula.

Figure 2:
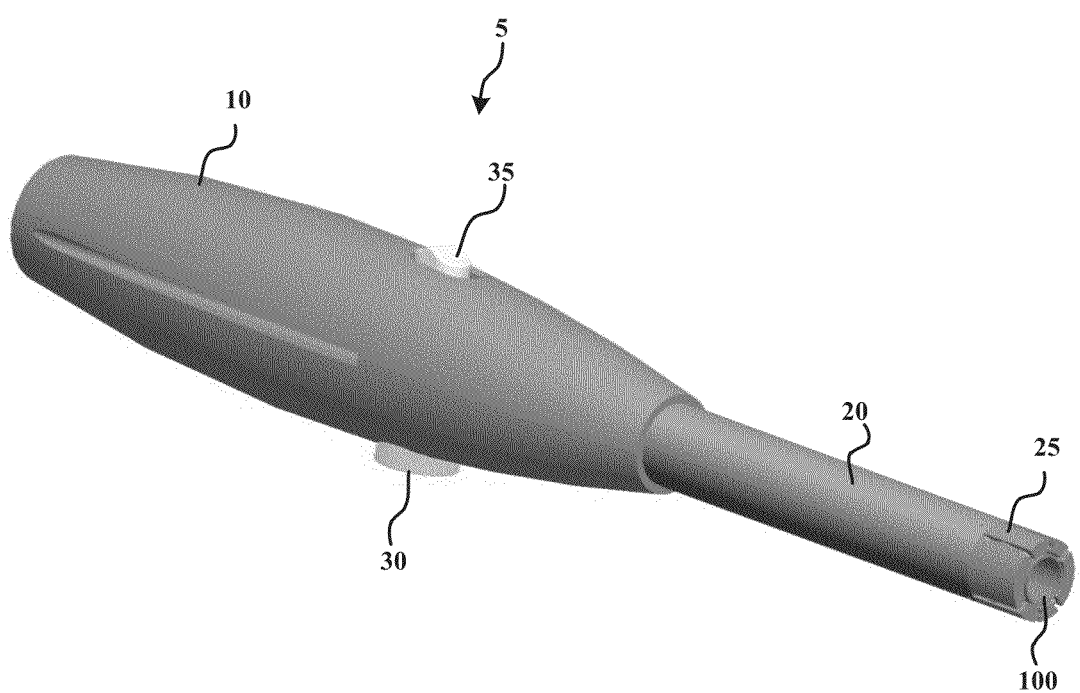

FIGS. 1 and 2 illustrate an example surgical closure device 5. The surgical closure device 5 includes a handle 10 configured to be held by an operator, e.g., a surgeon, to operate the surgical closure device 5 during a surgical procedure. A shaft 20 extends distally from the handle 10 and includes a distal end portion 25. An outer working tube 100 is disposed in a bore of the shaft 20 and extends concentrically along the longitudinal axis x of the shaft 20. The outer working tube 100 is distally exposed through an opening in the shaft 20. The outer working tube 100 has an outer diameter that is smaller than an inner diameter of the shaft 20, thus allowing the outer working tube 100 to be slidable along the longitudinal axis x. Although each of the outer working tube 100 and the shaft 20 are configured as right circular cylinders with concentric through bores, it should be understood that the outer working tube 100 and/or the shaft 20 may be provided with any appropriate geometry, e.g., a cross-section that is oval, polygonal, etc. and/or a cross-section that varies along the longitudinal axis x. Further, the geometry of the bore may differ substantially from the outer geometry for the outer working tube 100 and/or the shaft 20.

Referring to the inset partial view in FIG. 1, the distal end portion 25 of the shaft 20 includes six notches or slots 26, which extend from the distal tip of the shaft 20 a proximal distance along the longitudinal axis x. The slots 26 may be formed in any suitable manner, e.g., making three cuts in the distal end portion 25, each cut forming two of the slots 26 on opposed sides of the axis x. The dimensions of the slots 26 are selected to allow six respective anchors 200 to be disposed in the slots 26. In this regard, the wall thickness of the shaft (i.e., the distance between the bore and the outer surface) and the width of each slot 26 may be selected to be slightly greater than a respective lateral dimension of the anchor 200. Where the anchor 200 has a radial projection, the width of the slot 26 may be less than a diameter of the anchor through the projection. Thus, the geometry of the slot 26 may require that the anchor 200 be oriented such that the radial projection is at least approximately aligned with the longitudinal axis x of the shaft 20, since the anchor 200 would not otherwise fit into the slot 26.

Figure 3:
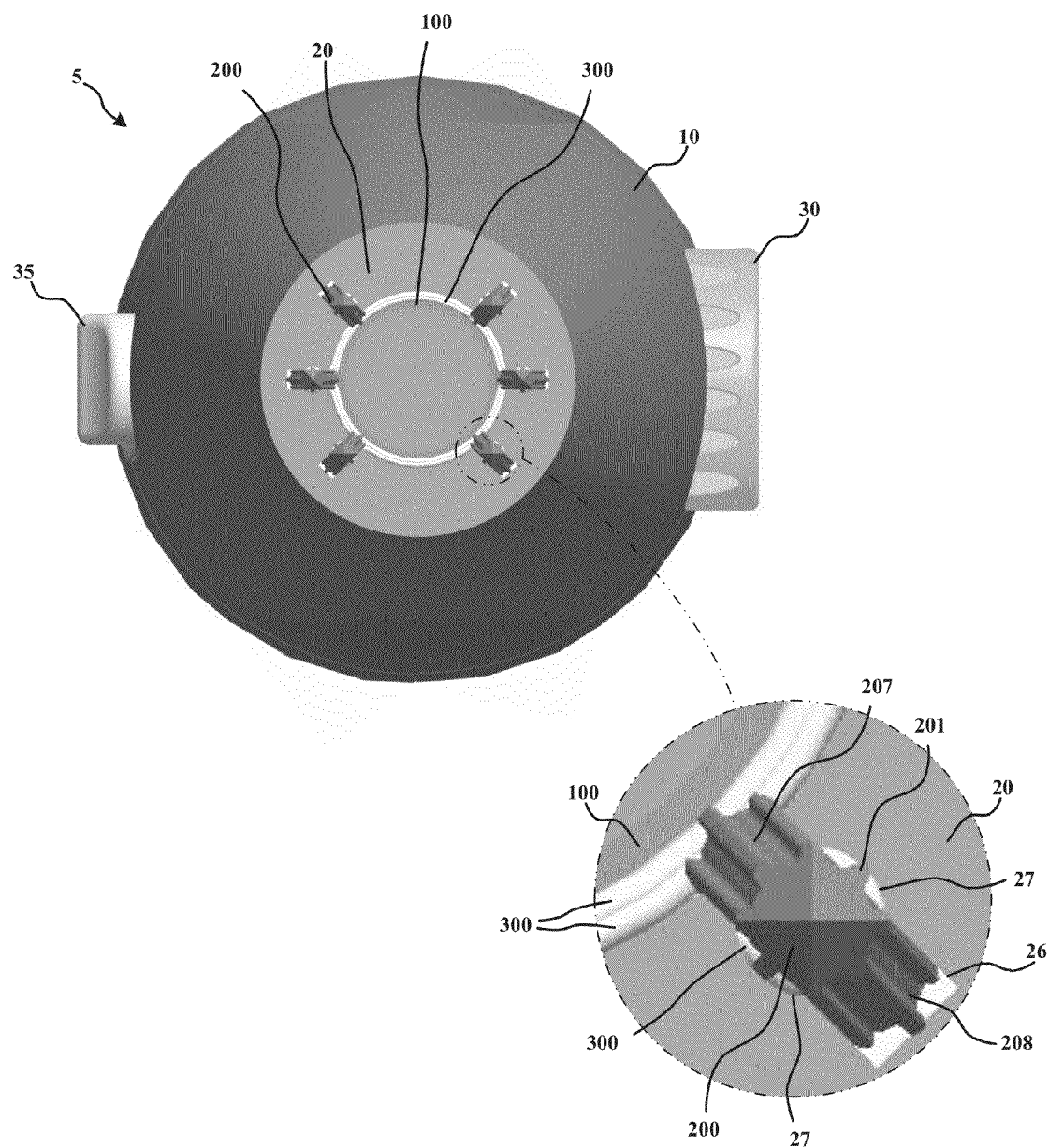
FIG. 3 is a front view with an inset partial front view of the surgical closure device of FIG. 1.

FIG. 3 is a front view of the surgical closure device 5. The slots 26, with respective anchors 200, are non-uniformly spaced apart along the circumferential periphery of the shaft 20. In particular, two groups of slots 26 are provided, one on the opposite side of the axis x from the other. Each of the two groups includes three slots 26 equally spaced apart. The circumferential spacing between the groups is greater than the circumferential spacing between the individual slots 26 in each group.

Referring to the inset partial view in FIG. 3, the slots 26 include side walls with opposed, longitudinally extending cylindrical grooves 27 for receiving the body 201 of the anchor 200. Further, the closure element 300 attached to the anchor 200 is able to pass along the cylindrical grooves 27. The slots 26 are also elongated in the radial direction to accommodate wings 207 and 208, which are described in greater detail below with regard to FIG. 4. Further, there is a gap between the outer working tube 100 and the end portion 25 of the shaft 20 to allow the closure elements 300 to be disposed therebetween as illustrated in FIG. 3.

Figure 4:
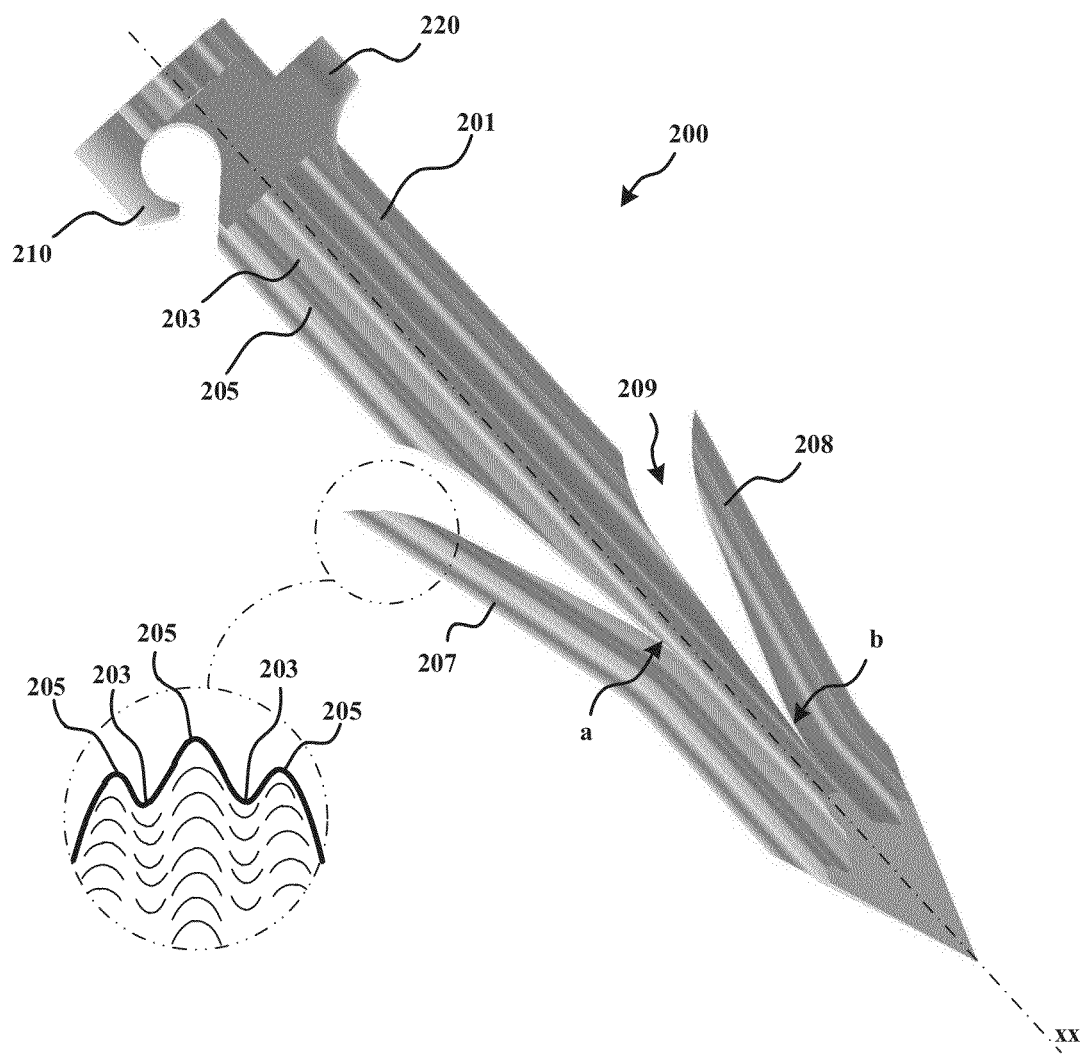
FIG. 4 shows an anchor of the self-acting closure arrangement of the device of FIG. 1.

FIG. 4 shows an anchor or implant 200 which is configured to be driven into a tissue. The anchor 200 includes a corrugated body 201. The body 201 includes grooves 203 that extend axially along the length of the body 201. Thus, extending circumferentially around the body 201, a plurality of grooves 203 alternate with a plurality of ridges 205. Further, the anchor body 201 includes a pair of wings or split portions 207 and 208. The split portions 207 and 208 are formed by respective splits or cuts 209 into the body 201. In this regard, the splits 209 may be formed by making a cut radially into the body 201 and extending in an axial direction. Thus, the two split portions 207 and 208 are attached to the remainder of the body 201 at a distal position and extend proximally to free ends. The free ends include a plurality of sharp protrusions along a curved surface. These points are formed due to the corrugations. In particular, the ridges 205 form the sharp protrusions, as illustrated in the inset partial side view in FIG. 4, which are advantageous for gripping tissue and preventing distal sliding of the anchor 200. Although each split portion 207 and 208 includes three such protrusions as illustrated, it should be understood that the anchor 200 may be designed such that one or more of the split portions has any other number of protrusions, including a single sharp protrusion. For example, if a larger number of sharp protrusions are desired, the body 201 could be more densely corrugated (i.e., a greater number of alternating grooves 203 and ridges 205 could be provided) and/or the angle of the cut or slice could be adjusted. Further, the length of proximal extension of the projections may be adjusted by varying the depth of the grooves 203 with respect to the ridges 205.

The split portions 207 and 208 do not substantially impede distal insertion into tissue but resist proximal movement from an insertion location by engaging the tissue. It has been discovered that the combination of the pointed and/or sharp-edged proximal ends of the split portions 207 and 208 with the alternating ridges on the proximal end of the split portions creates improved performance.

Further, the split portions or wings 207 and 208 are axially offset from each other. For example, split 207 is axially located at position a along axis xx and split 208 is axially located at position b along axis xx. This allows for greater structural strength of the other portions of the body 201 as compared to a non-offset configuration. In particular, since the cuts progress continually radially inward as they progress distally, a non-offset portion would have a substantially smaller amount of material in cross-section at the distal end of the cut. This would lead to a mechanically weak point or region along the axis of the body and could lead to mechanical failure, especially in anchors of small dimensions.

Although the anchors 200 utilize a pair of wings 207 and 208 to anchor the anchors 200 against proximal retraction from a tissue, it should be appreciated that any number of wings may be provided, and that as an alternative or in addition to the wings 207 and 208, any other appropriate anchoring structure(s), e.g., anchoring filaments, may be provided.

The distal tip of the anchor 200 is pyramidal, with a sharp point, and a plurality of surfaces separated by edges that converge at the sharp point. Although four planar surfaces are provided, it should be appreciated that any appropriate suitable number of surfaces may be provided and that one or more or all of the surfaces may be non-planar.

The anchor 200 also includes a hooked end portion 210. The hooked portion 210 is configured to receive one or more closure elements 300. On the side of the anchor 200 opposite the hooked portion 210 is an alignment projection 220 configured to rotationally align the anchor 200 about its longitudinal axis xx. Although the anchors 200 in the illustrated examples are aligned with the alignment projection 220 and the split portions 207 and 208 being intersected by and aligned along a plane containing the longitudinal axis x of the shaft 20 and the longitudinal axis xx of the anchor 200, it should be understood that the alignment projection 220 and the split portions 207 and 208 may be intersected by and aligned along a plane that contains the longitudinal axis xx of the anchor 200 and is transverse, e.g., perpendicular, to the plane containing the longitudinal axis x of the shaft 20 and the longitudinal axis xx of the device 20. Further, the alignment projection may be provided at any appropriate location around the circumference of the anchor 200 relative to the split portions 207 and 208 and that any appropriate number of alignment projections 220 may be provided for a particular anchor 200.

Although the anchor 200 is shown in the exemplary illustrations with closure elements 300, it should be understood that the anchor 200 may be used in connection with any other closure elements, including, e.g., closure elements 1300, 2300 described in greater detail below.

The anchor 200 may be produced by first forming the body 201 with the corrugations, e.g., by injection molding or extrusion, and subsequently forming split portions 207 and 208, e.g., by cutting radially into the side of the body 201. As illustrated, the cut is curved, with an angle (at the proximal entry point), relative to the longitudinal axis xx of the body 201, that gradually decreases from the proximal initial cutting location toward the distal end of the anchor 200 and eventually becoming linear. Although the split or cut of the illustrated example is made with a curved or varying angle with respect to the longitudinal axis xx of the body 201, it should be understood that any appropriate cut, including a linear cut, may be made.

Although the anchor 200 includes two wings or split portions spaced equally around the radial periphery of the body 201, it should be appreciated that any number of split portions, including a single split portion may be provided and at any appropriate spacing around the radial periphery of the anchor 200.

Modern manufacturing processes allow for near nano technology applications. This allows the anchors 200 to be manufactured in a size and complexity that may not have been possible in years past. The anchor 200 may be injection molded of either absorbable or non absorbable polymers and then processed (e.g., by cutting) to add the features of the wings 207 and 208. Although the anchors 200 are formed of polymer, it should be appreciated that any appropriate material may used, e.g., metal or a composite material. The anchors 200 may have a diameter of, e.g., one millimeter, or approximately one millimeter, and a length that is in a range from, e.g., 5 millimeters to 10 millimeters. According to some example embodiments, the diameter is less than one millimeter. According to some example embodiments, the diameter is in a range from 0.8 millimeters to 1.2 millimeters. It should be understood, however, that other dimensions may be provided.

Figure 5A:
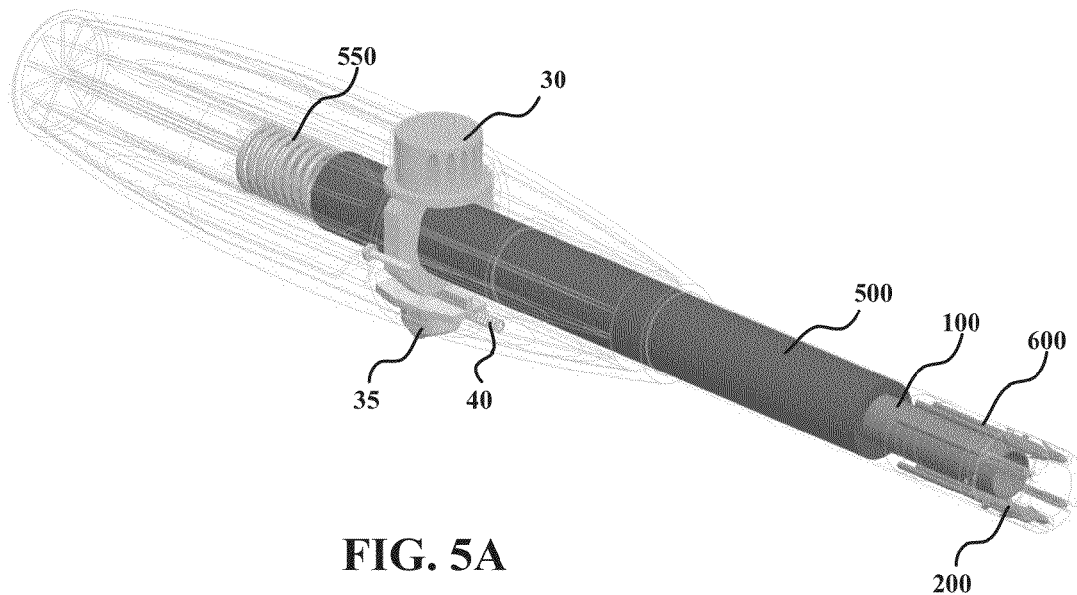
FIG. 5A shows a subassembly of the surgical closure device of FIG. 1.
Figure 5B:
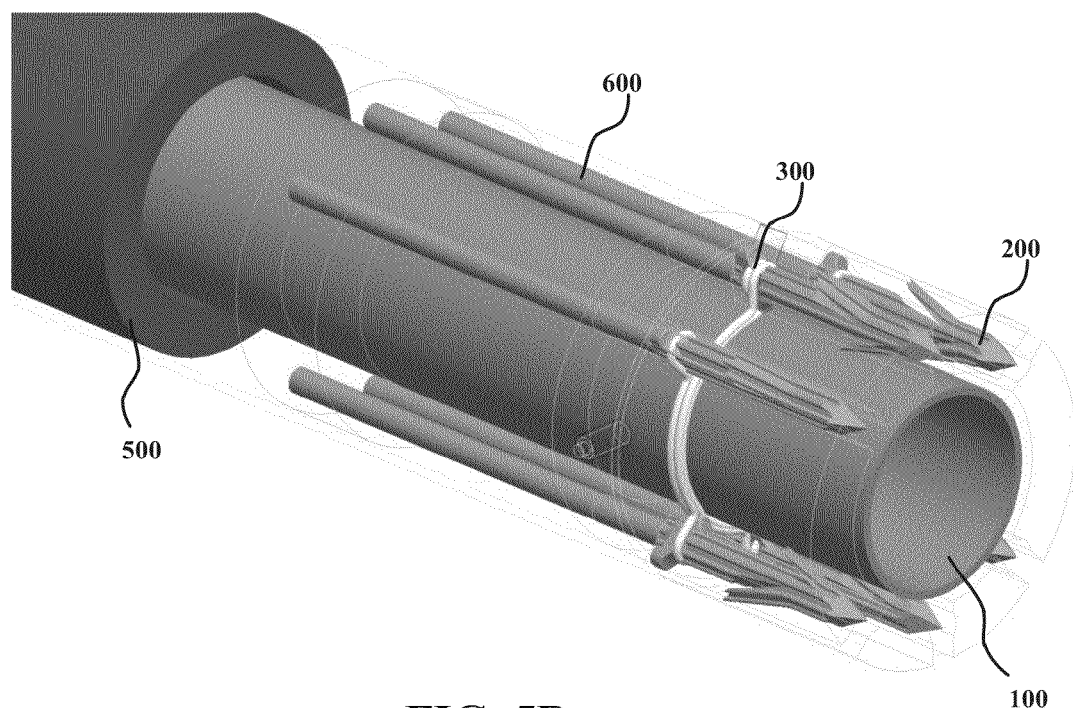
FIG. 5B is a partial view of the subassembly of FIG. 4.
Figure 5C:
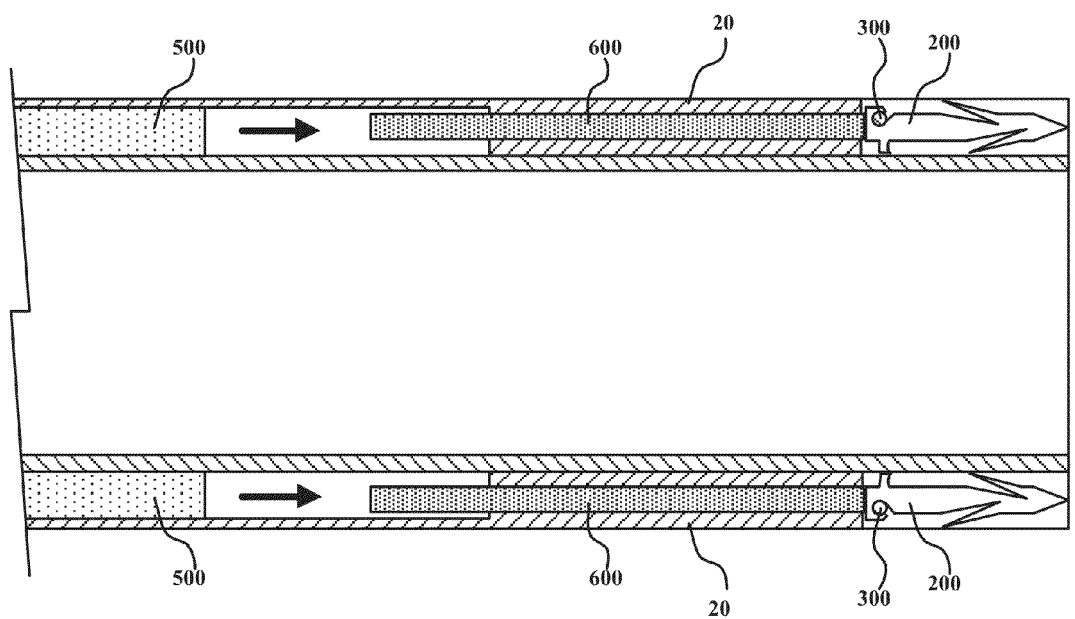
FIG. 5C is a partial sectional view of the device of FIG. 1 taken through a plane containing the longitudinal axis of the device and bisecting two opposed anchors.
Figure 6A:
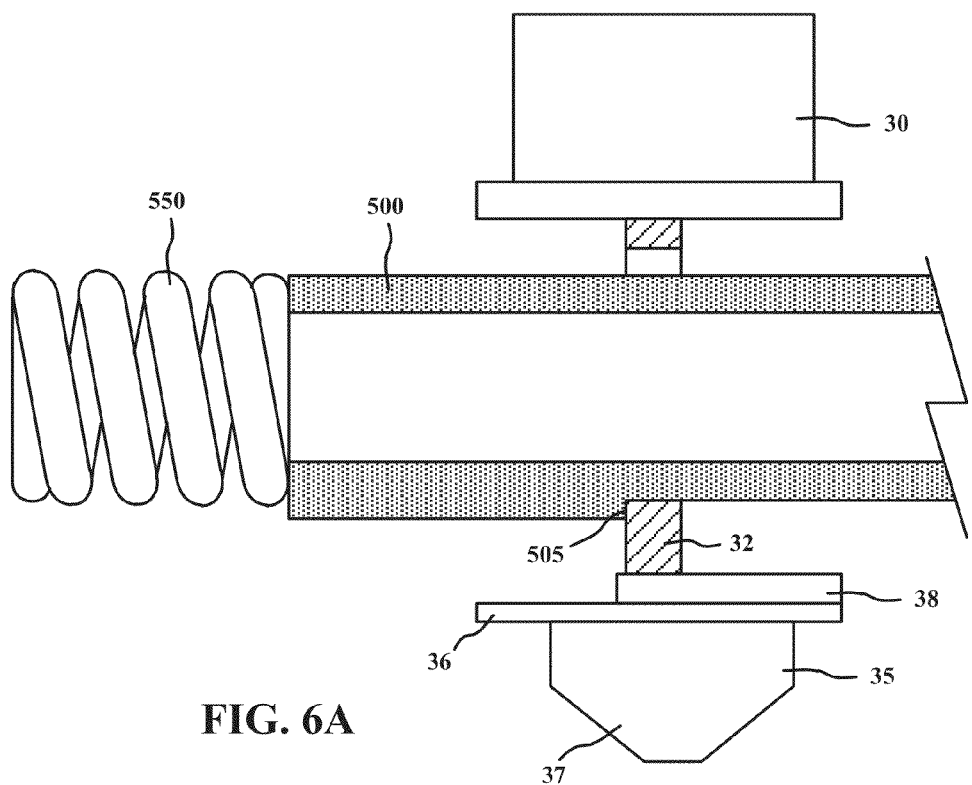
FIG. 6A is a partial cross-sectional view of the subassembly of FIG. 5A with a safety mechanism engaged.
Figure 6B:
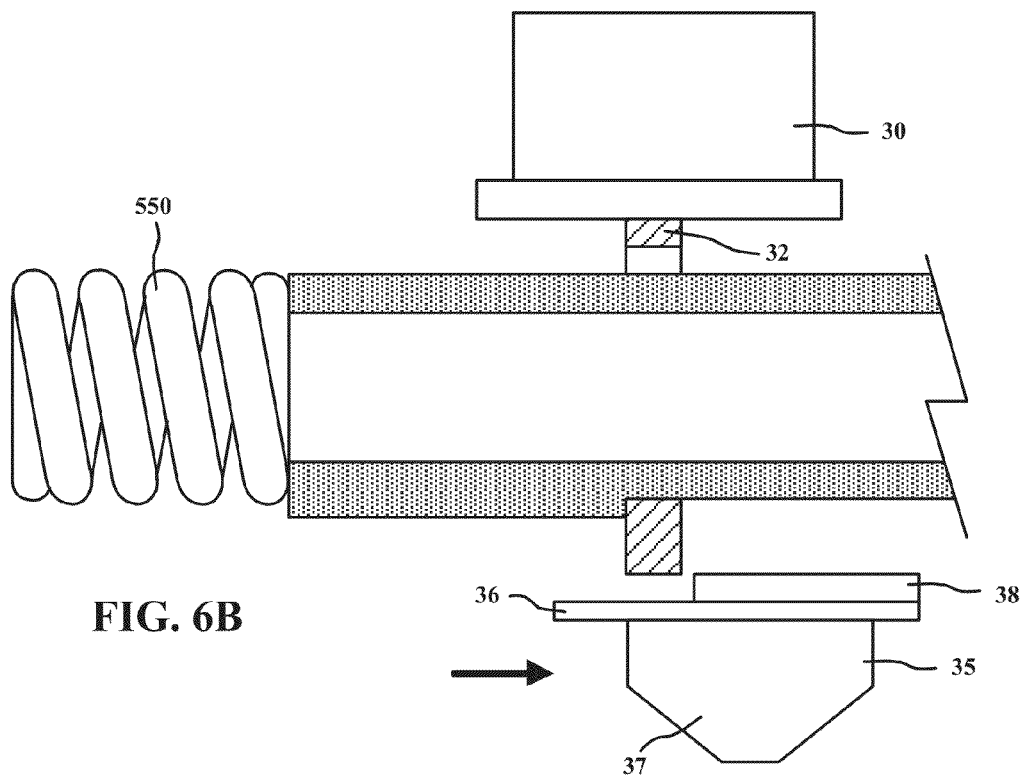
FIG. 6B is a partial cross-sectional view of the subassembly of FIG. 5A with the safety mechanism disengaged.
Figure 6C:
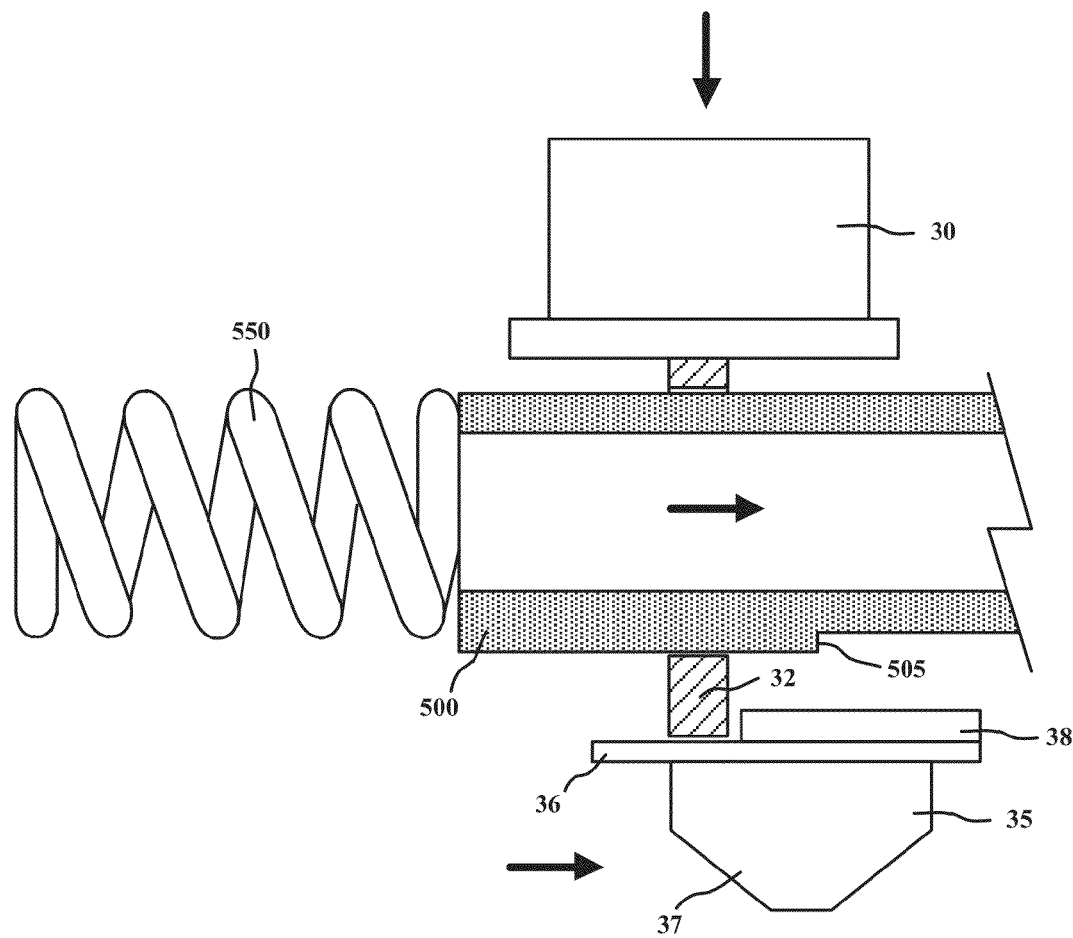
FIG. 6C is a partial cross-sectional view of the subassembly of FIG. 5A when a trigger is in a depressed state.

FIG. 5 shows a subassembly of the surgical closure device 5. The subassembly includes the trigger 30, the safety slide 35, a safety slide bias spring 40, a hammer sleeve 500, a driving spring 550, anvil pins 600, the outer working sleeve 100, and anchors 200. In the state illustrated in FIG. 5, the surgical closure device 5 is loaded and ready to be actuated in order to drive the anchors 200. In this regard, a proximal end of the hammer sleeve 500 contacts a distal end of the driving spring 550, which is in a compressed state as illustrated in FIG. 5. To maintain the hammer sleeve 500 in its proximal position while the compressed driving spring 550 applies a distally directed force, the hammer sleeve 500 latches with a trigger plate 32 of the trigger 30, as schematically illustrated in FIG. 6A. In FIGS. 6A to 6C, the hammer sleeve 500 and the trigger plate 32 are shown in cross-section to facilitate illustration. To latch the hammer sleeve 500, the hammer sleeve 500 is pushed proximally, while the trigger 30 is in a depressed state (such as illustrated in FIG. 6C) until a lip or step proximally clears the proximal side of the trigger plate 32. The trigger 32 is then moved (e.g., via a spring bias force and/or manually) to a non-depressed position, as illustrated in FIG. 6A. The trigger moves in a transverse direction between the depressed and non-depressed positions by sliding within lateral channels in the housing of the handle 10. However, any appropriate guiding mechanism may be provided.

To maintain the trigger 32 in the non-depressed position in order to prevent or reduce the likelihood of accidental driving of the anchors 200 (e.g., due to user error, during shipping, storage, etc.), the safety slide includes a safety rib or bar 38 which, as illustrated in FIG. 6A, is positioned adjacent the trigger plate 32 to form a positive or hard stop, thereby obstructing movement of the trigger 30 from the non-depressed position of FIG. 6A to the depressed position of FIG. 6C. As illustrated, e.g., in FIG. 6A, the safety slide 35 includes a pair of lateral projections 36 configured to longitudinally slide within a corresponding channel in the housing of the handle 10. It should be understood, however, that any appropriate guide mechanism may be provided. The safety slide 35 also includes a knob portion 37 to facilitate sliding of the safety slide 35 using, e.g., one of the operator's fingers.

When the operator desires to drive the anchors 200, the operator must first move the safety slide 35 into a driving position in which the safety bar 38 does not obstruct movement of the trigger plate 32. Referring to FIG. 5, the safety slide is urged or biased toward the proximal safety position by a compression spring 40. Thus, the operator must continuously apply a force to the knob 37 until the bottom of the trigger plate 32 moves to a position that prevents or blocks the safety bar 38 from returning to the safety position. This may provide for even greater safety, since the operator must generally coordinate the holding of the safety slide 35 in the driving position while depressing the trigger 30. It should be understood, however, that the safety slide 35 may be configured to remain in the driving position without continuous application of force. Further, it should be understood that the device 5 may be provided without any safety mechanism.

FIG. 6B shows safety slide 35 in the driving position. Although the safety slide is moved distally, i.e., in the direction of the arrow shown in FIG. 6B, it should be understood that the safety switch may be configured to move in any suitable direction to move between safety and firing positions. After the safety slide 35 is moved to the driving position shown in FIG. 6B, the operator depresses the trigger 30, e.g., with one of the operator's fingers, until the lower portion of the trigger plate 32 clears the step 505 of the hammer sleeve 500, thereby releasing the hammer sleeve 500 for distal movement actuated by the compressed driving spring 550.

Referring, e.g., to the partial sectional view of FIG. 6B, the hammer sleeve 500 is spaced apart from the anvil pins 600 prior to depressing the trigger. The anvil pins 600 are slidable along the longitudinal axis x of the shaft 20 within respective bores of the shaft 20 corresponding to respective anchors 200. As the hammer sleeve 500 moves forward, it gains speed and momentum. Upon contact with the proximal ends of the anvil pins 600, the hammer sleeve 600 imparts a momentum to the anchors 200, since the distal ends of the anvil pins 600 are in alignment with the proximal ends of the anchors 200. In this manner, the anchors 200 are driven at a substantial speed, which facilitates driving of the anchors 200 into soft tissue.

The anchors are preferably driven at a speed greater than 50 meters per second, more preferably in a range of 50 to 350 meters per second, and most preferably at 350 meters per second. However, it should be understood that the anchors 200 may be driven at any suitable speed sufficient for the anchors to puncture tissue.

Further, the anchors 200 may be driven into a single layer or multiple layers of tissue and that the speed may be selected based on the structural properties, dimensions, and relative locations of the one or more tissues into which the anchors are driven.

In order to accurately penetrate soft tissues that are not held or secured on a distal side, a rapid penetration of each layer of tissue may be required in order to effect penetration of the tissue layer or layers. If an anchor 200 is applied slowly, the tissue or tissues may be pushed distally away by the anchor 200 without adequate penetration. Thus, some example delivery mechanisms eject each implant at a relatively high speed, as set forth above. Although the example device 5 utilizes a spring-loaded mechanical driving mechanism, it should be understood that other drivers may be provided. In some examples, saline is used to pressurize a channel within a catheter, needle, or other tube at such a rate that a plunger will eject the anchor at the precise speed. Further example embodiments push the anchors using long push rods which run the length of a catheter or other tube. The ejection modality may be computer-controlled and/or operator-controlled. For example, as with the spring loaded mechanical system of the illustrated examples, an ejection force may be predetermined and repeatable by an operator's actuation of a trigger 30.

Moreover, the driver may be configured to drive the anchors 200 to a predetermined depth. Although the illustrated examples control the depth by contact between closure elements 300 (described in greater detail below), which are coupled to the anchors 200, and flanges or flared portions 405, any other depth-controlling mechanism may additionally or alternatively be provided. For example, the precision of the depth may be accomplished by a precise hydraulic driving force, engagement with other stops, or a suture that tautens to limit the depth. Further, the depth may be monitored using fluoroscopy or any other appropriate imaging mechanism. The driving mechanism may include pressurized saline or other hydraulic fluid that is pressurized through the thoracoscopic catheter shaft. Thus, very precise control may be accomplished.

FIG. 6 is an enlarged partial view of the subassembly of FIG. 4. As illustrated, a plurality of closure elements 300 are coupled to the hook portions 210 of the anchors 200. There are four closure elements 300, each of which is coupled to the hook portions 210 of exactly two anchors 200. Thus, as illustrated, e.g., in FIG. 10, two anchors 200 are attached to exactly two different closure elements 300 and four anchors 200 are attached to exactly one closure element 300. It should be understood, however, that other arrangements may be provided.

Figure 7:
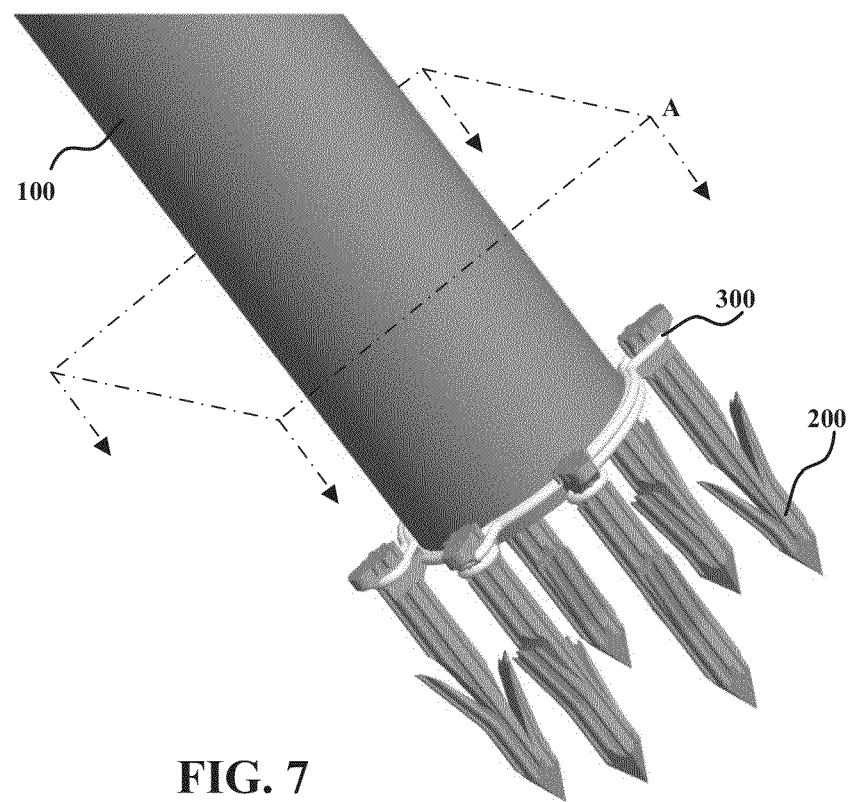
FIG. 7 is a partial view of the working tube and a self-acting closure arrangement of the surgical closure device of FIG. 1.

FIG. 7 is a partial view of the working tube 100, the anchors 200, and the closure elements 300. As illustrated in FIG. 7, the anchors 200 have been driven, e.g., into tissue. The anchors 200 and the closure elements 300 form a self-acting closure arrangement of the surgical closure device 5. During driving of the anchors 200, the closure elements 300 are also driven an analogous distance due to the engagement of the closure elements 300 with the anchors 200.

Figure 8A:
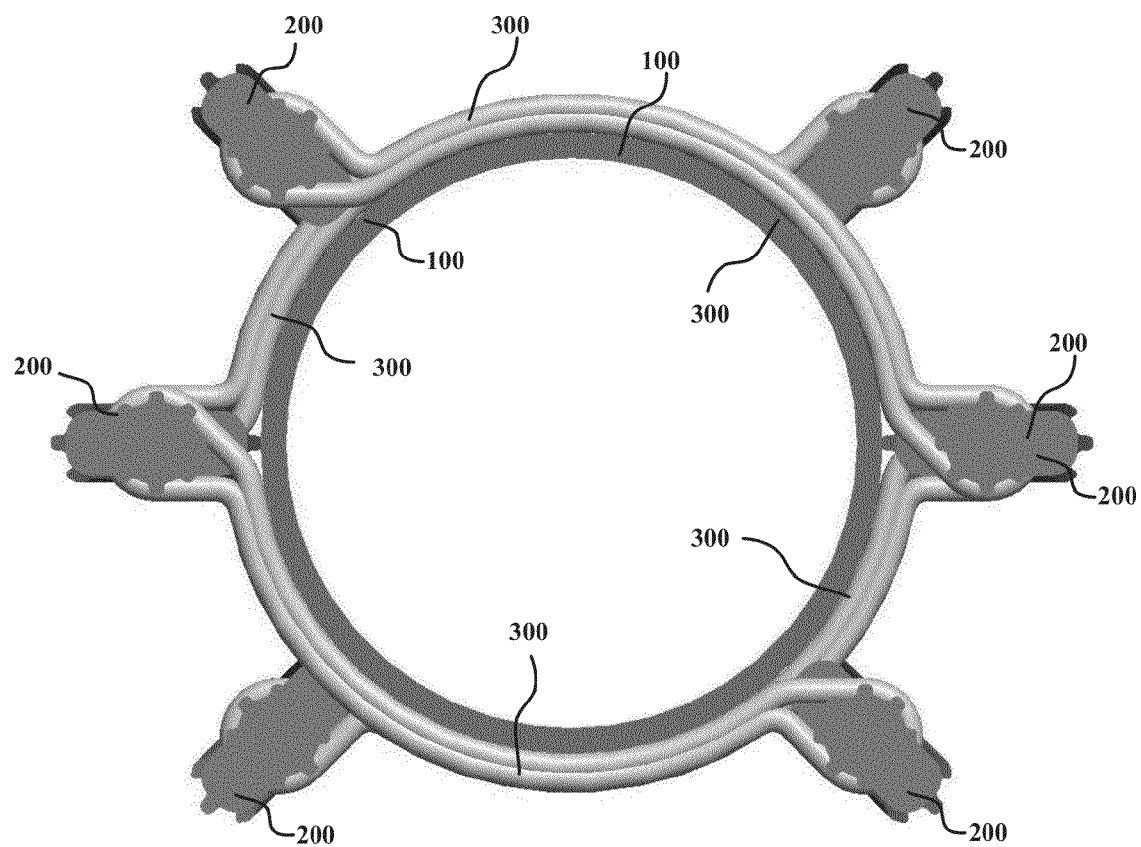
FIG. 8A is a cross-sectional view according to plane A of FIG. 7.

Referring to the cross-sectional view of FIG. 8A, the closure elements 300 are layered and are held along the periphery of the outer working tube 100, thereby preventing the closure elements 300 from pulling the anchors 200 toward each other.

Figure 8B:
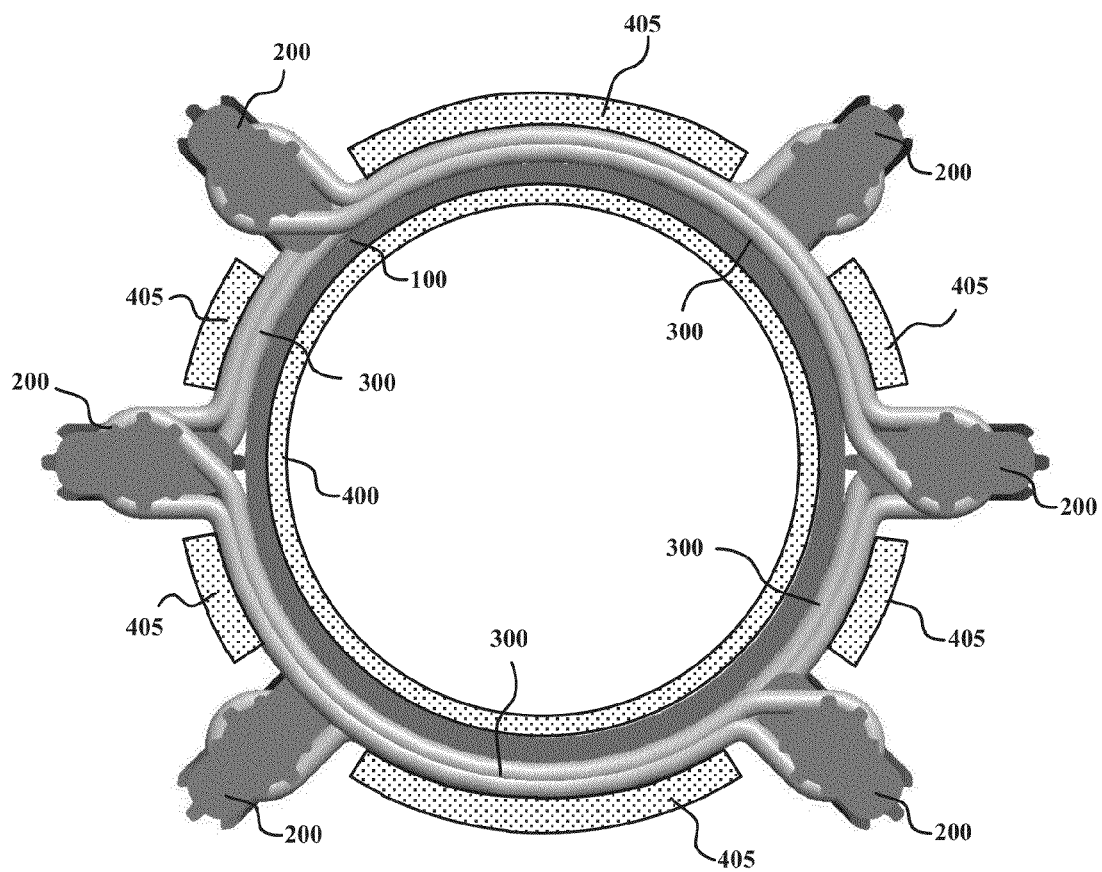
FIG. 8B is a cross-sectional view according to plane A of FIG. 7 when a cannula is disposed in the outer working tube.
Figure 8C:
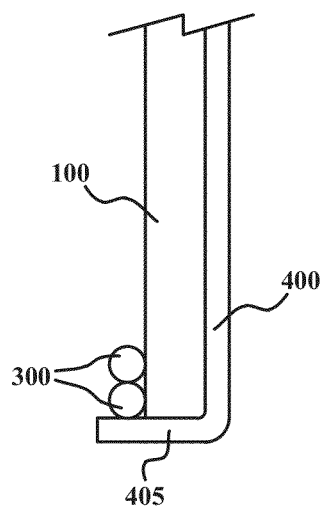
FIGS. 8C, 8D, and 8E sequentially and schematically illustrate the retraction of the cannula of FIG. 8B with respect to the outer working tube and the release of the closure elements.

FIG. 8B is the same as FIG. 8A, except that a cannula 400 is disposed within the outer working tube 100. The elements shown in FIG. 8B may be separated from the remainder of the surgical device 5 to allow a surgical procedure to be conducted. For example, a trocar may be inserted longitudinally through the interior of the cannula 400 to pierce the tissue at a location encircled by the anchors 200 that are anchored into the tissue. The piercing of the tissue may provide access to the opposed side of the tissue (e.g., the interior of a viscus such as the heart, etc.) by thoracoscopic or other surgical instruments.

The cannula 400 includes six radially extending flared portions or flats 405. The cannula 400 extends concentrically within the outer working tube 100. The cannula 400 extends distally beyond the distal end of the outer working tube 100 such that the flats 404 fold over the distal end of the outer working tube 100. The radial extension of the flats 405 beyond the circumferential periphery of the outer working tube 100 allows the flats 405 to form positive or hard stops that prevent or resist the closure elements 300 from inadvertently sliding off the end of the outer working tube 100, e.g., during thoracoscopic procedures being performed with access through the cannula 400.

Figure 8D:
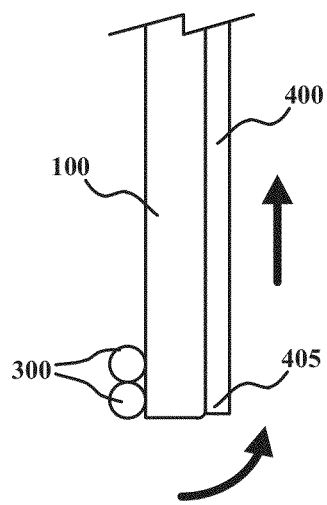
Figure 8E:
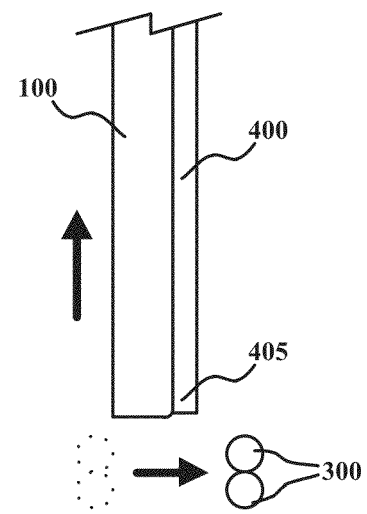

When the procedure no longer requires access through the cannula 400, any surgical instruments may be refracted via the cannula 400 from the viscus being operated upon. At this stage, the hole in the tissue formed by the trocar should be closed. In order to do so, the cannula 400 is moved relative to the outer working tube 100, as illustrated sequentially in FIGS. 8C and 8D. In doing so, the flats 405, which are formed as leaf springs, rotate to a longitudinal orientation and are retracted. Thus, the flats 405 no longer form stops against distal sliding of the closure elements 300 along the outer working tube 100. This orientation is illustrated in FIG. 8D. The flats 405 may be formed of any suitable material, e.g., a shape memory material such as nitinol, spring steel, etc.

The flats 405 may be bistable, with two rest orientation: one corresponding to the radially flared orientation, and the other corresponding to the longitudinal orientation.

After the flats are retracted, the cannula 400 and the outer working tube 100 are proximally refracted from the surgical entry site. Since the closure elements 300 are engaged with the hooked portions 210 of the anchors 200, which are anchored into the tissue against proximal retraction, the closure elements remain adjacent the surgical closure site. Thus, the proximal retraction of the cannula 400 and the outer working tube 100 causes the outer working tube 100 to slide distally with respect to the closure elements 300. Further distal retraction of the cannula 400 and outer working tube 100 causes the closure elements 300 to slip off of the distal end of the outer working tube 100, thereby entirely disengaging the closure tubes 300, as well as the anchors 200, from the cannula 400 and working tube 100. Since the closure elements 300 are pre-tensioned, they pull the anchors 200 toward the hole formed at the surgical entry location. Since the anchors 200 are anchored into the tissue surrounding the hole, the pulling of the anchors into approximation causes the surrounding tissue to be pulled toward the hole. Thus, the hole is squeezed shut, with the closure elements 300 maintaining a closure force to keep the hole closed.

Figure 9A:
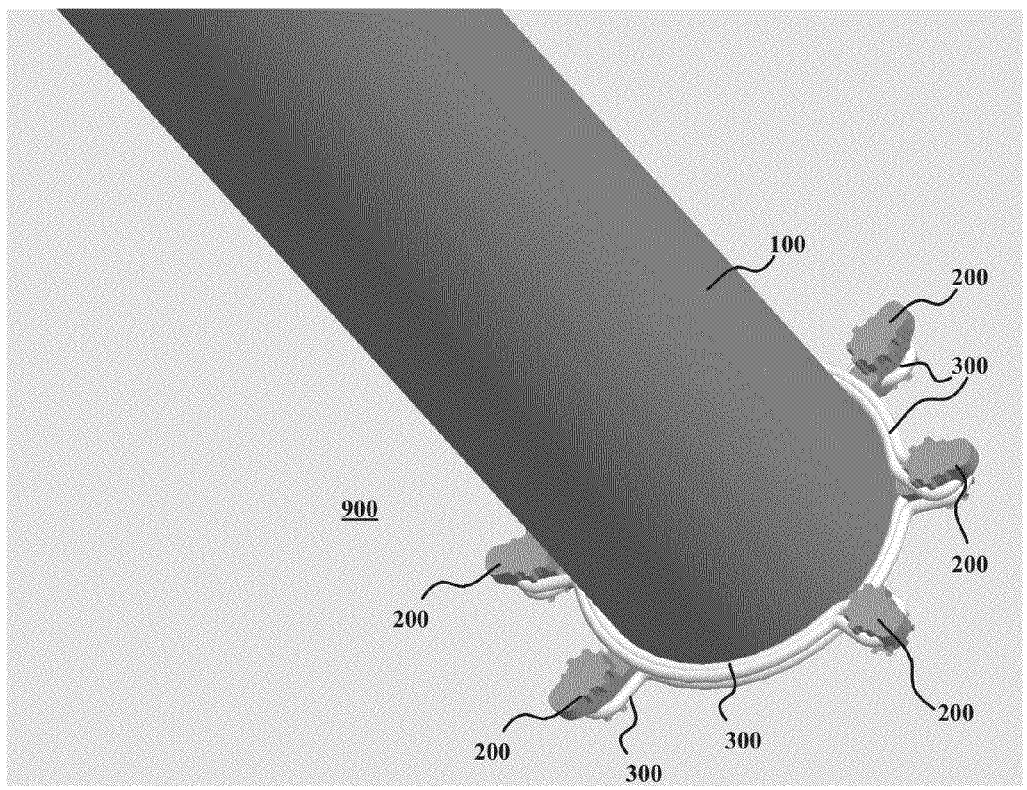
FIG. 9A is a partial view of the outer working tube of the device of FIG. 1 with the self-acting closure arrangement inserted into a tissue.
Figure 9B:
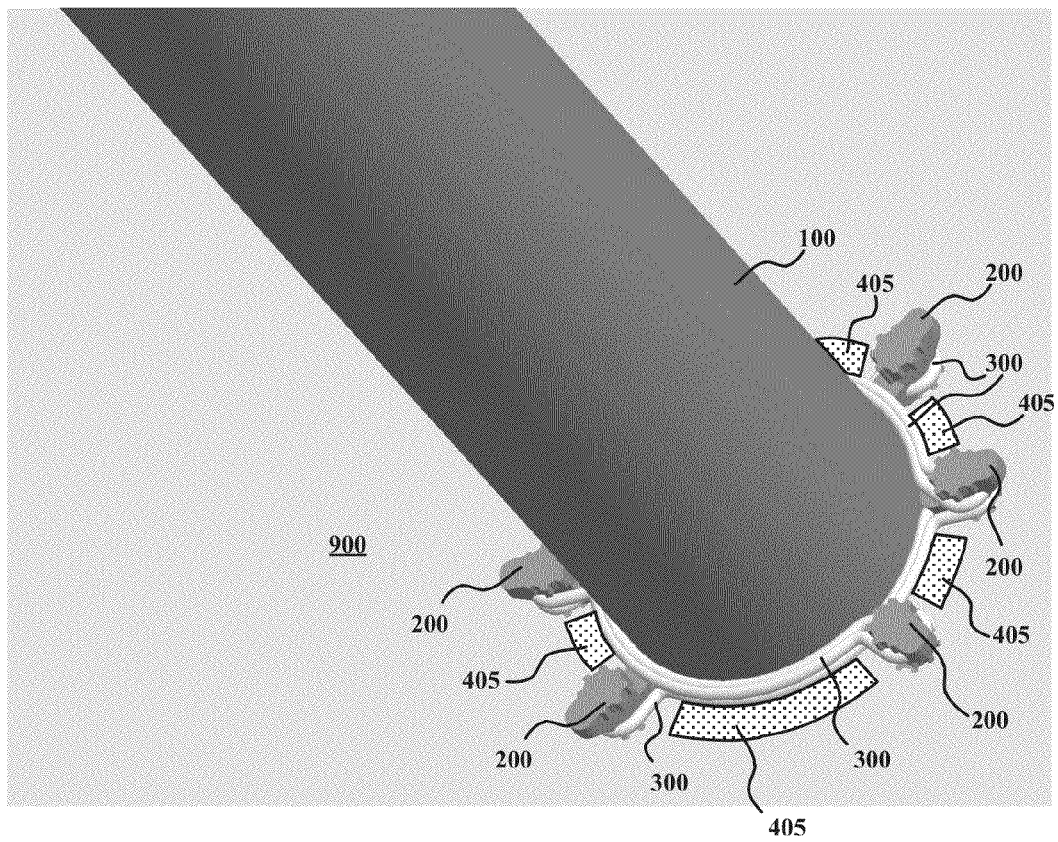
FIG. 9B is a partial view of the outer working tube and a cannula with the self-acting closure arrangement of the device of FIG. 1 inserted into a tissue.

FIG. 9A is a partial view of the outer working tube 100 with the anchors 200 inserted into the tissue 900. FIG. 9B is the same as FIG. 9B but schematically shows the flats 405, which extend between the outer working tube 100 and the closure elements 300 to prevent the closure elements 300 from causing premature or inadvertent closure of entry opening in the tissue. FIG. 9B may be a working arrangement, whereby the portions of the surgical device 5 other than the cannula 400, the outer working tube 100, the anchors 200, and the closure elements 300 are removed. Thus, various other surgical instruments, e.g., thoracoscopic surgical devices, may be maneuvered through the interior of the cannula 400 and the working tube 100.

Figure 10A:
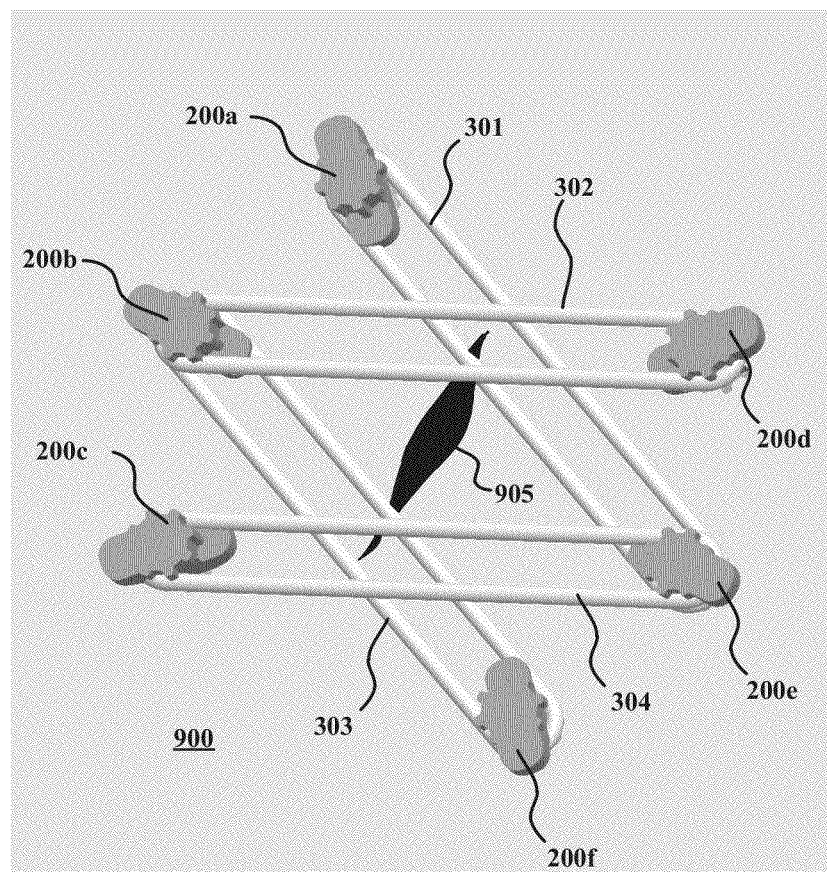
FIG. 10A shows the self-acting closure arrangement of the device of FIG. 1 inserted in the tissue after removal of the cannula and working tube.

FIG. 10A shows the self-acting closure arrangement, in this case the anchors 200 and the closure elements 300, inserted in the tissue after removal of the cannula 400 and working tube 100. For illustration purposes, the anchors 200 are shown in their initial driven positions in the tissue 900. In other words, for ease of illustration, the arrangement is illustrated as though the anchors 200 are being prevented from being pulled together by the closure elements 300. The anchors 200 are disposed around a surgical entry opening 905, such as formed, e.g., by a trocar.

The anchors 200 are arranged in two opposed groups of anchors. To facilitate the description of the arrangement shown in FIG. 10A, the anchors 200 are provided individual reference numbers 200a, 200b, 200c, 200d, 200e, and 200f. The first group includes anchors 200a, 200b, and 200c, and the second group includes anchors 200d, 200e, and 200f. Each of the anchors in each group is connected by a closure element 300 directly to at least one anchor of the other group. Further, no two anchors within either group are directly connected to each other by a closure element. That is, each closure element 300 is connected at one end to an anchor of the first group 200a, 200b, 200c and at the other end to an anchor of the second group 200d, 200e, 200f. Thus, the forces exerted by the elements 300 are primarily directed in a direction from one group toward the other group.

It is further seen from FIG. 10A that the anchor/closure element arrangement is configured as two opposed and overlapping V-shaped groups. The first V-shaped group is formed of anchors 200a, 200e, 200c and closure elements 301, 304. The second V-shaped group is formed of anchors 200d, 200b, 200f and closure elements 302, 303.

Figure 10B:
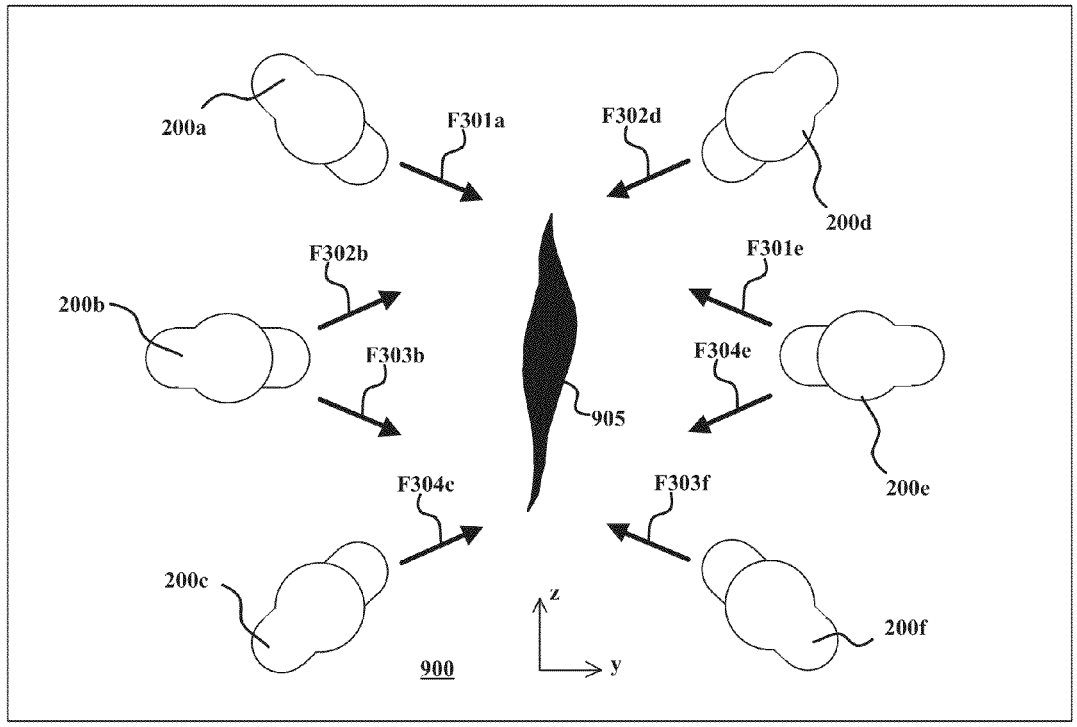
FIGS. 10B and 10C schematically illustrate the forces exerted by the anchors of FIG. 10A.

Since each closure element is wrapped around two anchors and forms a single complete loop, the force exerted by the respective closure element at each anchor is equal to the sum of the tension forces in the two band portions extending between the two anchors to which the closure element is connected. Moreover, the force is exerted along a line extending between the two anchors to which the closure element is connected. In this regard, the forces exerted at the locations of the anchors 200a, 200b, 200c, 200d, 200e, 200f are illustrated in FIG. 10B by arrows F301a, F301e, F302b, F302d, F303b, F303f, F304c, and F304e which represent respective force vectors. In particular, F301a represents the force exerted by closure element 301 at the anchored location of anchor 200a, F301e represents the force exerted by closure element 301 at the anchored location of anchor 200e, F302b represents the force exerted by closure element 302 at the anchored location of anchor 200b, F302d represents the force exerted by closure element 302 at the anchored location of anchor 200d, F303b represents the force exerted by closure element 303 at the anchored location of anchor 200b, F303f represents the force exerted by closure element 303 at the anchored location of anchor 200f, F304c represents the force exerted by closure element 304 at the anchored location of anchor 200c, and F304e represents the force exerted by closure element 304 at the anchored location of anchor 200e. Further, the forces form three pairs of complementary forces that are equal and opposite to each other. In particular, a first pair F301a, F301e, a second pair F302b, F302d, a third pair F303b, F303f, and a fourth pair F304c, F304e. Each pair corresponds to a single closure element 301, 302, 303, 304, respectively and are directed in opposite directions along the extension of the respective closure element 301, 302, 303, 304 between the two anchors 200 to which the respective closure element 301, 302, 303, 304 is connected.

Since anchors 200a, 200c, 200d, 200f are each connected to a single closure element 301, 304, 302, 303, respectively, only a single force vector F301a, F304c, F302d, F303f, respectively, is shown in FIG. 10B. Since anchors 200b and 200e are each connected to two closure elements, two force vectors are associated with each of anchors 200b and 200e in FIG. 10B. That is, anchor 200b, which is connected to closure elements 302 and 303, has two force vectors F302b and F303b acting through the anchored location of anchor 200b, and anchor 200e, which is connected to closure elements 301 and 304, has two force vectors F301e, F304e acting through the anchored location of anchor 200b.

Figure 10C:
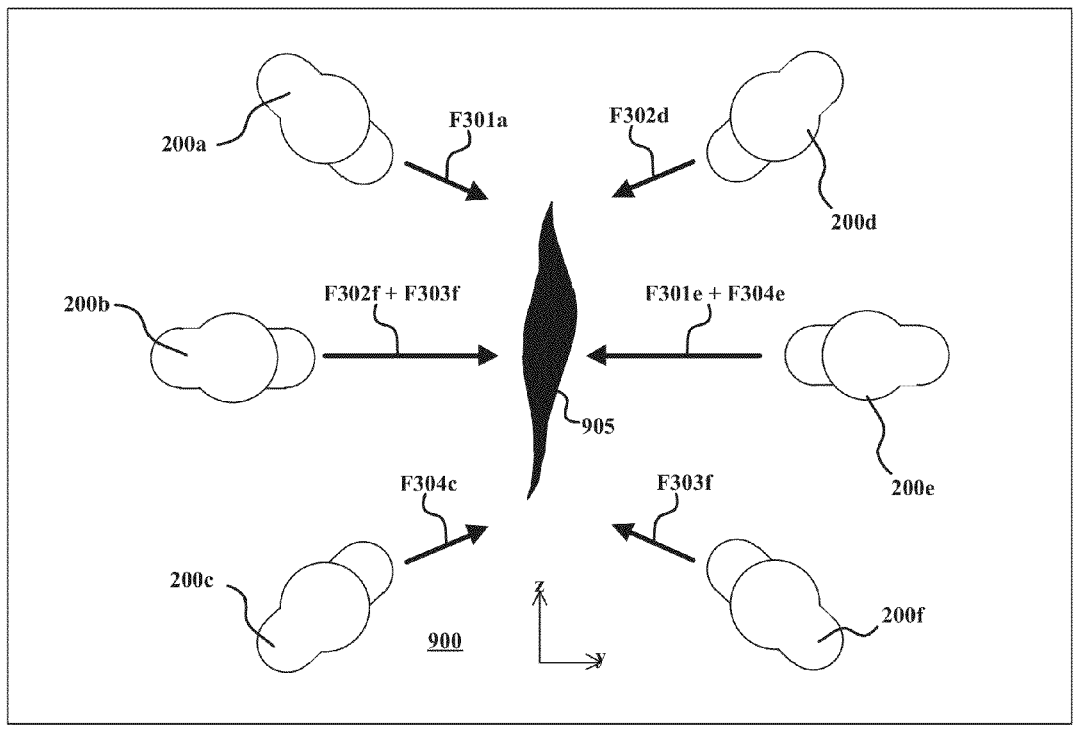

Since the forces represented by vectors F302b and F303b both act through the same location, i.e., the anchored location of the anchor 200b, the resultant force through the anchored location of anchor 200b may be determined as the sum of the two vectors F302b and F303b. Likewise, since the forces represented by vectors F301e and F304e both act through the anchored location of the anchor 200e, the resultant force through the anchored location of anchor 200b may be determined as the sum of the two vectors F302b and F303b. Accordingly, FIG. 10C schematically illustrates the total forces exerted by the closure elements on each anchor, with the force exerted through anchor 200b represented by the resultant vector F302f+F303f and the force exerted through anchor 200e represented by the resultant vector F301e+F304e.

Due to the positioning of the anchors 200a, 200b, 200c, 200d, 200e, 200f and the arrangement of the closure elements 301, 302, 303, 304, a greater amount of compressive force is exerted in the direction of a y axis than a z axis. The z axis corresponds to a line that extends between the first group of anchors 200a, 200b, 200c and the second group of anchors 200d, 200e, 200f and is at least approximately equidistant from the first group of anchors 200a, 200b, 200c and the second group of anchors 200d, 200e, 200f. The y axis is perpendicular to the z axis, and both the x axis and the y axis extend along the surface of the tissue 900.

Figure 10D:
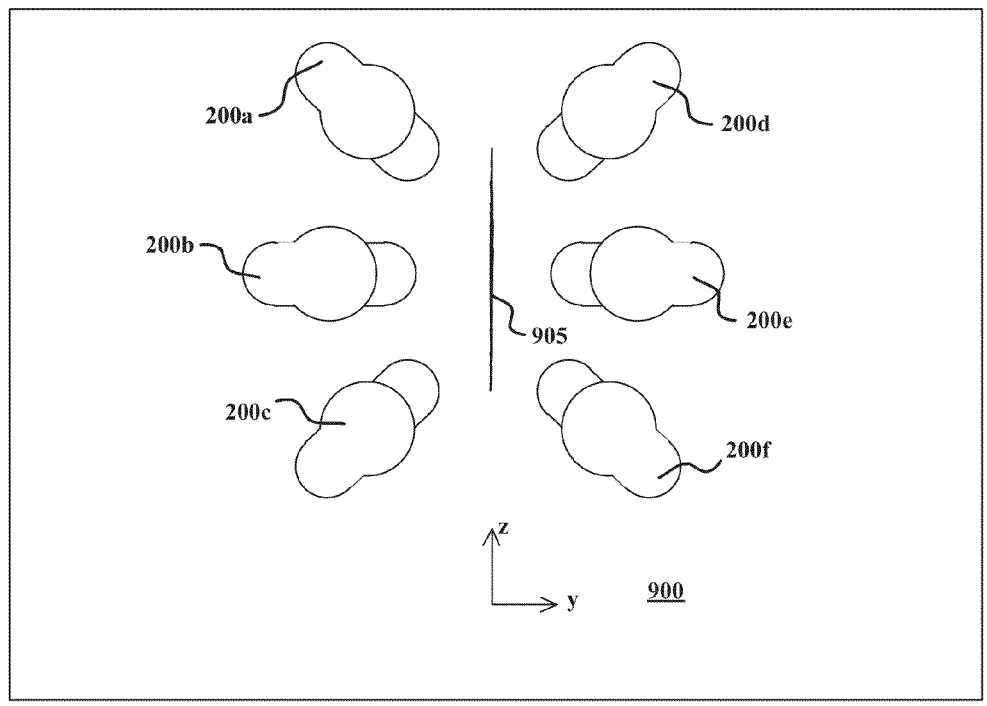
FIGS. 10D and 10E illustrate the anchors of FIG. 10A when drawn to their closed or approximated positions to close a hole in a tissue.

Since compressive force is greater in directions parallel to the x axis than in directions parallel to the z axis, the self-acting closure formed by the anchors 200a, 200b, 200c, 200d, 200e, 200f and the closure elements 301, 302, 303, 304 tends to close the opening 905 such that the opening 905 is flattened or elongated along the z axis, as illustrated in closure of FIG. 10D. This may be desirable to maintain a more reliable closure that is more resistant to leaking.

Figure 10E:
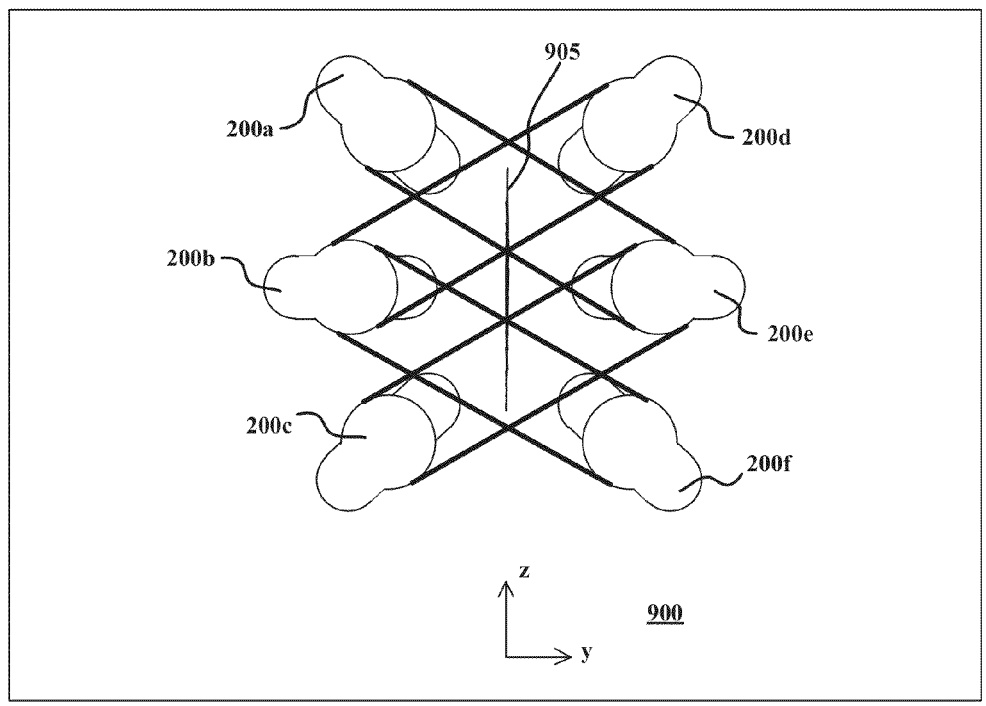

As schematically illustrated in FIG. 10D, the anchors 200a, 200b, 200c, 200d, 200e, 200f have been drawn into their closed or approximated positions, thereby pulling the tissue, to which they are anchored, toward the opening 905, thereby closing the opening 905 as illustrated. To facilitate illustration, the closure elements 301, 302, 303, 304 are not shown in FIG. 10D. However, FIG. 10E shows the closure of 10D with the closure elements 301, 302, 303, 304. The forces being exerted by the closure elements 301, 302, 303, 304 on the anchors 200a, 200b, 200c, 200d, 200e, 200f are analogous to those illustrated in FIGS. 10B and 10C. However, since the exemplary closure elements 301, 302, 303, 304 are have a spring-like elasticity, the force exerted by the closure elements 301, 302, 303, 304 may be reduced as the anchors 200a, 200b, 200c, 200d, 200e, 200f are drawn into approximation.

In the resting closure position (i.e., the position at which the anchors 200a, 200b, 200c, 200d, 200e, 200f settle after transient movement from the orientation around the working tube 100) illustrated in FIGS. 10D and 10E, the force exerted by the closure elements 301, 302, 303, 304 through each anchor 200a, 200b, 200c, 200d, 200e, 200f is equal to an oppositely directed resistance force exerted onto the anchors 200a, 200b, 200c, 200d, 200e, 200f by the tissue at the respective location of each anchor 200a, 200b, 200c, 200d, 200e, 200f.

Figure 11:
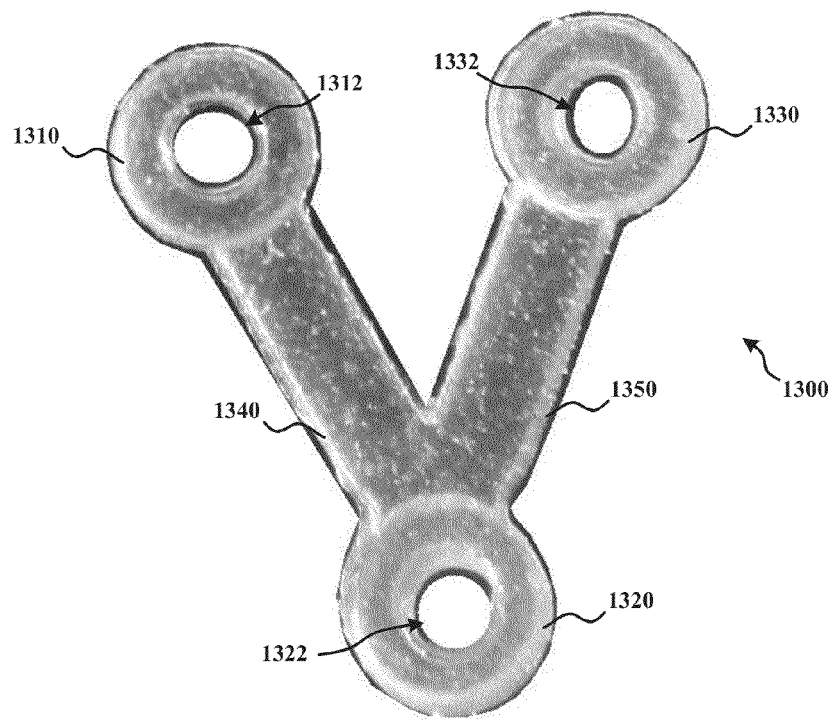
FIG. 11 shows a closure element with a V-shaped configuration in accordance with an example embodiment of the present invention.

FIG. 11 shows another closure element 1300. The closure element 1300 includes three anchor-receiving portions 1310, 1320, 1330 arranged in a V-shaped configuration with portion 1320 being disposed at the vertex. Arm 1340 spans directly from anchor-receiving portion 1310 to anchor-receiving portion 1320, and arm 1350 spans directly from anchor-receiving portion 1320 to anchor-receiving portion 1330. The anchor-receiving portions 1310, 1320, 1330 each have a respective aperture 1312, 1322, 1332 for receiving a respective anchor, e.g., the anchor 200 described above or the anchor 1200 described in greater detail below with respect to FIG. 13. The anchor-receiving portions 1310, 1320, 1330 are each toroidal in shape and have a greater material thickness than the arms 1340 and 1350. It should be understood, however, that any appropriate geometry may be provided and that any appropriate material thickness may be provided. The toroidal shape of the anchor-receiving portions 1310, 1320, 1330 couple with the anchors 200, 1200 in a manner analogous to the band-shaped closure elements 300 described above with regard to anchor 200.

The closure element 1300 functions in the same manner described above with regard to the closure elements 300, but differs in that only two closure elements are required to generate the same forces illustrated in FIGS. 10B and 10C. In particular, the closure element 1300 performs the same function as the two closure elements 301, 304, or the two closure elements 302, 303 of the second V-shaped groups described above with respect to FIG. 10A. Further, the closure element 1300 differs in that a single structural element, i.e., each of arms 1320, extends between opposed anchors.

Figure 12:
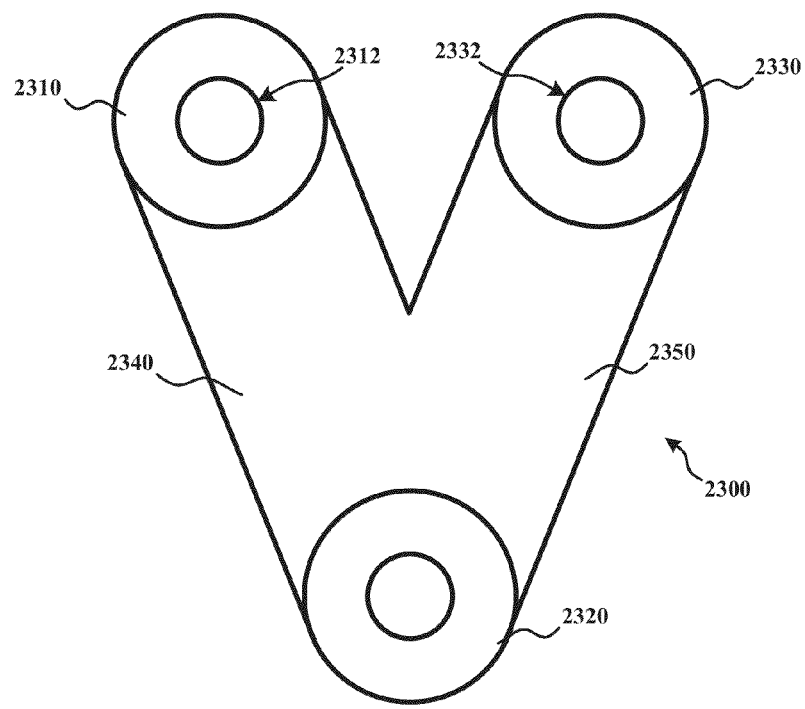
FIG. 12 shows another V-shaped closure element in accordance with an example embodiment of the present invention.

FIG. 12 shows another closure element 2300, which includes three anchor-receiving portions 2310, 2320, 2330 arranged in a V-shaped configuration with portion 2320 being disposed at the vertex. Arm 2340 spans directly from anchor-receiving portion 2310 to anchor-receiving portion 2320, and arm 2350 spans directly from anchor-receiving portion 2320 to anchor-receiving portion 2330. The anchor-receiving portions 2310, 2320, 2330 each have a respective aperture 2312, 2322, 2332 for receiving a respective anchor. The anchor 2300 includes all of the features described above with respect to anchor 1300, but differs only in that the Arms 2340, 2350 have are widened to be substantially the same width as the outer diameter of each of the anchor-receiving portions 2310, 2320, 2330. This may be advantageous to provide additional strength and tension force when the arms 2340, 2350 are stretched.

Figure 13:
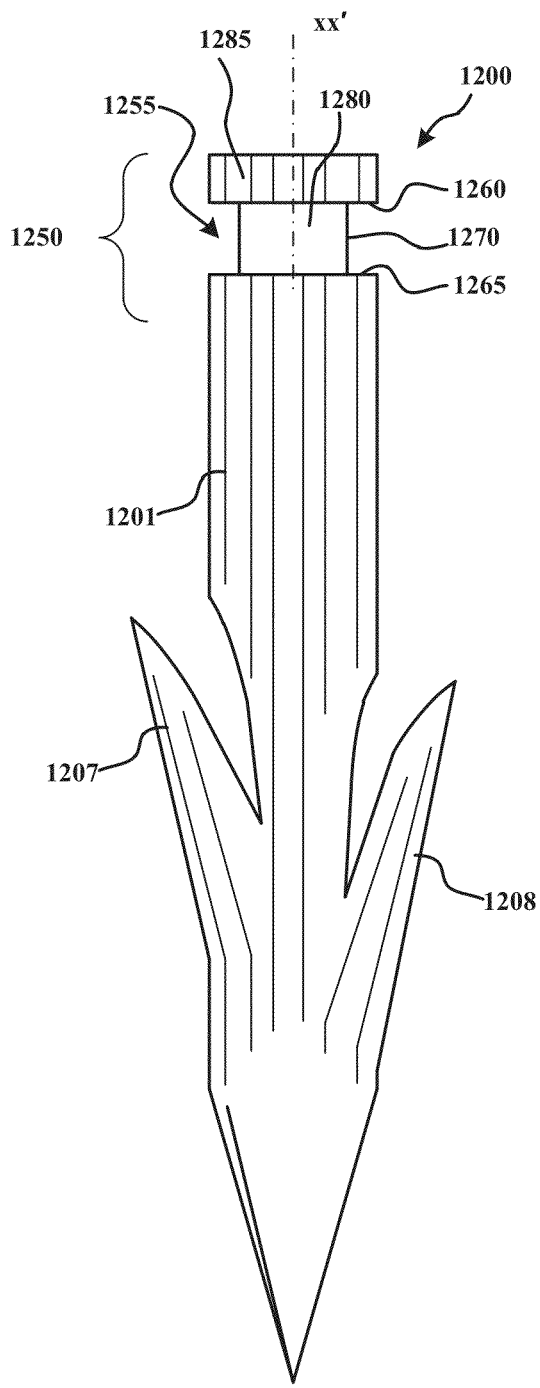
FIG. 13 shows an anchor in accordance with an example embodiment of the present invention.

FIG. 13 shows an anchor 1200. Anchor 1200 is identical to anchor 200 described above except that a proximal end portion 1250 includes a circumferential channel 1255 formed as a continuous radial recess extending around the entire circumference of the anchor 1200. The channel opens in the radial direction and includes a distally directed first surface 1260 and an opposed proximally directed second surface 1265. Extending between the first and second surfaces 1260 and 1265 is a surface 1270 corresponding to a reduced-diameter portion 1280 of the anchor 1200. Although the reduced-diameter portion 1280 is cylindrical and concentric with the longitudinal axis xx' of the anchor 1200, it should be understood that any appropriate geometry and orientation may be provided. For example, the reduced-diameter portion 1280 may be frustoconical and/or have a cross section that is curved when viewed in a direction perpendicular to the longitudinal axis xx' of the anchor 1200. Further, the surface 1270 of the reduced-diameter portion 1280 may vary along the circumference of the anchor 1200.

The circumferential channel 1255 axially separates a proximal head portion 1285 from the distal remainder of the body of the anchor 1200.

When one or more closure elements 300, 1300, 2300 is coupled to the anchor 1200, the first surface 1260 restrains the one or more closure elements 300, 1300, 2300 from proximally sliding beyond the channel 1255 and off the end of the anchor 1200. Likewise, the second surface 1265 restrains the one or more closure elements 300, 1300, 2300 from sliding distally beyond the channel 1255. In this regard, the dimensions of the channel 1265, e.g., the width and depth of the channel 1265, may be selected to accommodate a particular number of closure elements 300, 1300, 2300, or a single closure element 300, 1300, 2300.

A particular closure element 300, 1300, 2300 is mated to the anchor 1200 by mating placing the anchor 300, 1300, 2300 around the reduced-diameter portion 1280 of the anchor 1200. For example, an anchor-receiving portion 1310, 1320, 1330 of anchor 1300 and/or an anchor-receiving portion 2310, 2320, 2330 of anchor 2300 may be mated to the anchor 1200 stretching the respective anchor-receiving portion 1310, 1320, 1330, 2310, 2320, 2330 over the proximal head portion 1285 and onto the reduced-diameter portion 1280 of the anchor 1200. When mated in this manner, the reduced-diameter portion 1280 extends through the respective aperture 1312, 1322, 1332, 2312, 2322, 2332, with the anchor-receiving portion 1310, 1320, 1330, 2310, 2320, 2330 constrained between the first and second walls or surfaces 1260 and 1265 of the channel 1255. In this regard, the apertures 1312, 1322, 1332, 2312, 2322, 2332 may have resting diameters that are the same, larger, or smaller than the diameter of the reduced-diameter portion 1280. It may be advantageous, however, to provide a resting diameter that is less than the outer diameter of the first surface 1260, the second surface 1265, and/or the proximal head portion 1285 in order to resist inadvertent disengagement of the closure element 1300, 2300 from the anchor 1200.

The channel 1255 performs a function analogous to that of the hooked portion 210 described above with respect to Although the anchor 1200 does not include a hooked portion such as hooked portion 210 of anchor 200, it should be understood that one or more hooked portions may be provided in combination with the channel arrangement of anchor 1200.

Figure 14:
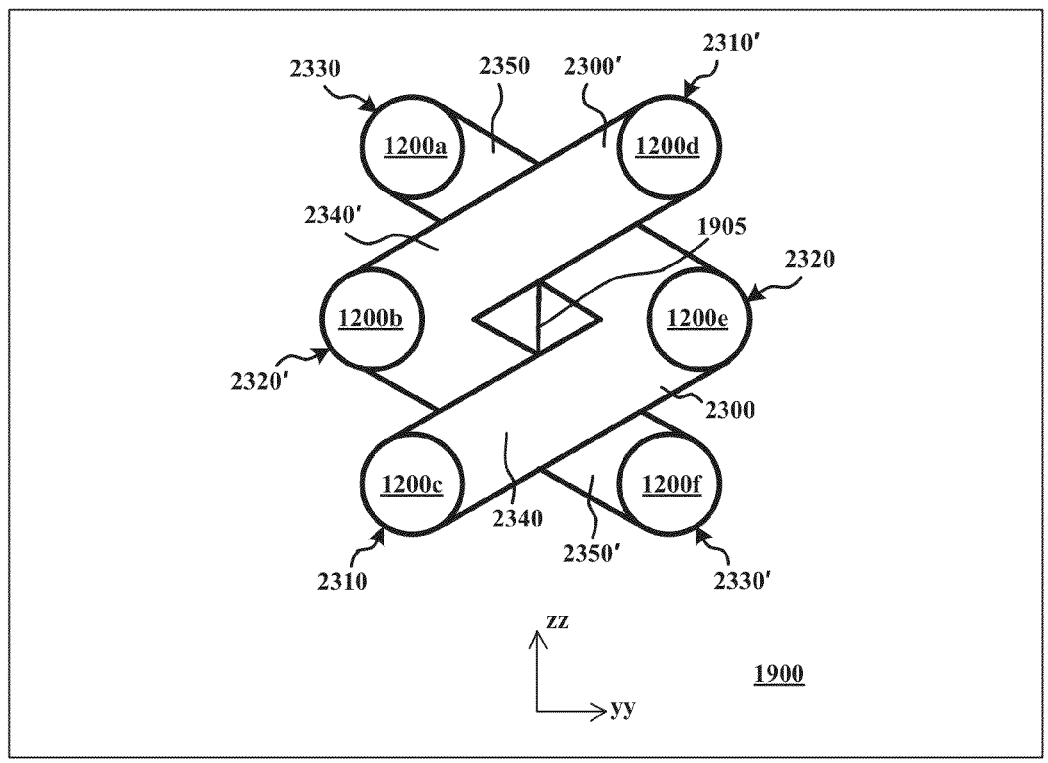
FIG. 14 shows a plurality of anchors of FIG. 13 and closure elements of FIG. 12 when closing a hole in a tissue.

FIG. 14 shows a plurality of anchors 1200 of FIG. 13 and closure elements 2300 of FIG. 12 when closing an hole 1905 in a tissue 1900. As with the example described above regarding anchors 200, individual instances of the anchor 1200 are denoted with lower-case letters. In this regard, anchors 1200*a*, 1200*b*, 1200*c*, 1200*d*, 1200*e*, and 1200*f* are arranged in the same configuration as described above with respect to anchors 200*a*, 1200*b*, 1200*c*, 1200*d*, 1200*e*, and 1200*f* and exert the same forces respectively. Axes yy and zz in FIG. 14 correspond to axes y and z described above.

In FIG. 14, there are first and second instances of closure element 2300, with the second instance being distinguished by like reference characters being followed with the character ' (prime). In comparison to the overlapping V-shaped arrangements shown in FIG. 10A, arm 2350 of FIG. 14 performs a function analogous to the closure element 301, arm 2340' performs a function analogous to the closure element 302, arm 2350' performs a function analogous to the closure element 303, and arm 2340 performs a function analogous to the closure element 304. Further, as with the arrangement of FIG. 10A, the two V-shaped arrangements are both overlapping and interlocking. That is, when viewed along a line normal to the surface of the tissue 900, 1900, each V-shaped arrangement of each configuration has a first extension that intersects on a proximal side of the respective opposed V-shaped configuration and a second extension that intersects on a distal side of the respective V-shaped configuration. Thus, referring to FIG. 10A, closure element 302 overlaps closure element 301 and closure element 304 overlaps closure element 303, with respect to the surface of the tissue 900. Likewise, referring to FIG. 14, arm 2340' overlaps arm 2350 and arm 2340 overlaps arm 2350'. It should be understood, however, that other configurations may be provided.

Figure 15:
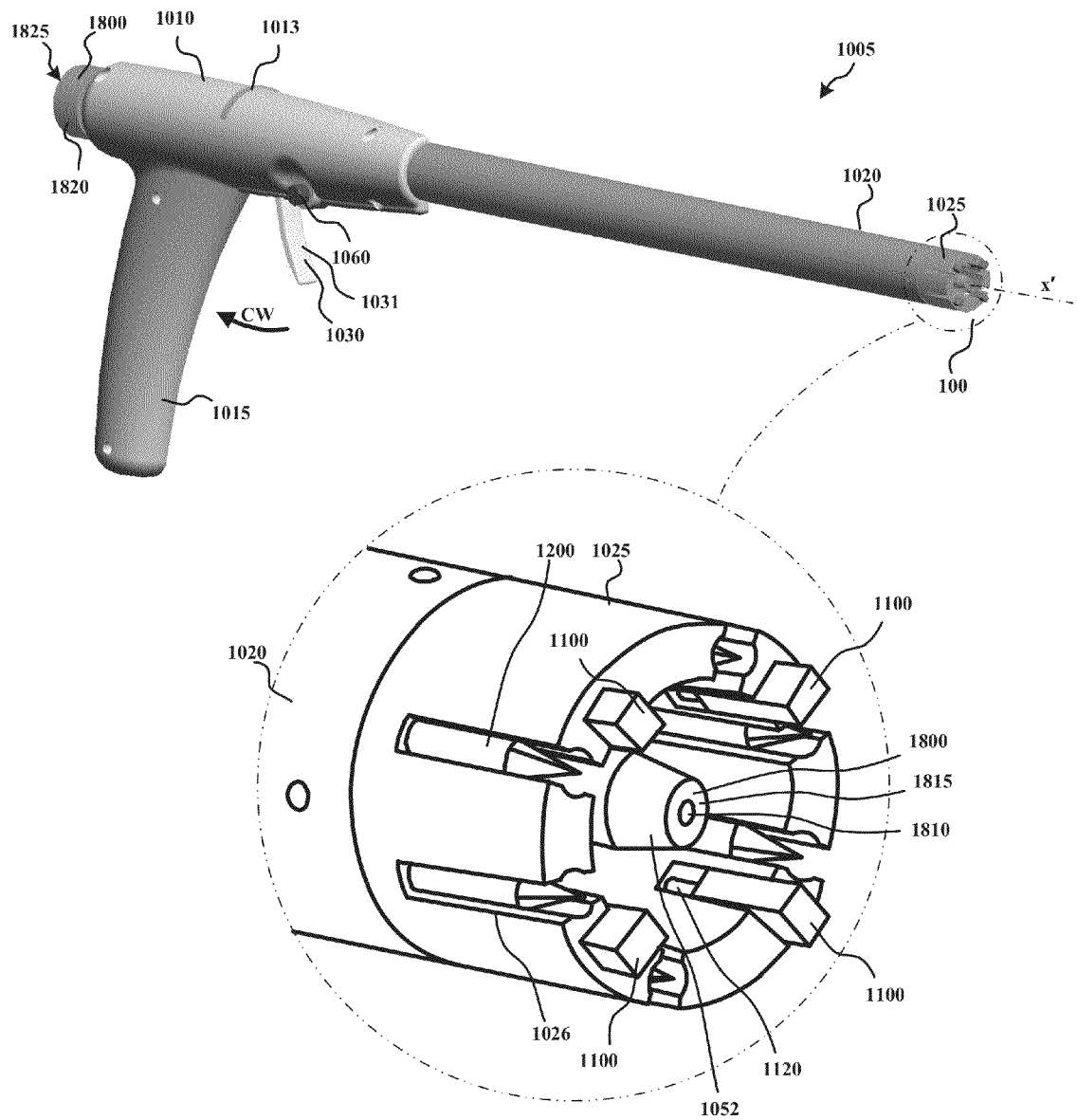
FIG. 15 shows a surgical closure device in accordance with an example embodiment of the present invention.

FIG. 15 shows a surgical closure device 1005 according to an example embodiment of the present invention. Except as indicated otherwise, the surgical closure device 1005 includes features that are the same or analogous to all of the features of the surgical device 5 described in greater detail above. Further, the features described with respect to surgical closure device 1005 may be provided in combination with any feature of surgical closure device 5.

The surgical closure device 1005 includes a handle 1010 including a pistol grip 1015 configured to be held by an operator, e.g., a surgeon, to operate the surgical closure device 1005 during a surgical procedure. A shaft 1020 extends distally from the handle 10 and includes a distal end portion 1025. Unlike the surgical closure device 5, the surgical closure device 1005 does not, at least initially, include an outer working tube or a cannula extending therewithin. Instead, the surgical closure device 1005 includes a centering mechanism 1800 in the form an elongated tubular shaft with a distal portion 1805 that tapers to have a reduced diameter at the a distal end of the centering mechanism 1800. An inner guide bore 1810 extends along the longitudinal axis of the centering mechanism 1800 from the distal end 1815 to the proximal end 1825 of the centering mechanism 1800. The longitudinal axis of the centering mechanism 1800 corresponds to the longitudinal axis x' of the shaft 1020 when the device is assemble in the state illustrated in FIG. 15.

The centering mechanism 1800 may be especially advantageous during "over the wire" surgical procedures such as pericardiocentesis. Some pericardiocentesis procedures involve inserting a needle, via an intercostal opening into the patient's thorax, into the pericardial sac, guiding a guide wire through the needle, and subsequent removal of the needle with the guide wire left in place. After removal the needle, a tapered dilator may be advanced over the guide wire to dilate the opening in the pericardium tissue. The dilated opening, or tract, allows room for a catheter. After the dilation, the catheter is guided over the guide wire into the pericardial sac to drain fluid from the pericardium.

Referring the device 1005, after the flexible guide wire is placed at the desired location in the pericardial sac and needle has been withdrawn, the free proximal end of the guide wire is introduced into the distal opening of the guide bore 1810 and extended entirely through the guide bore 1810 until the guide wire extends from the proximal end portion 1820. The device 1005 is then guided into the patient's body to the location of the pericardial tissue by distally sliding along the guide wire extending through the guide bore 1810. Once positioned such that the distal end portion 1025 of the shaft 1020 abuts the tissue, six anchors 1200 are driven into the tissue in the same general manner described above with regard to the anchors 200.

Figure 16:
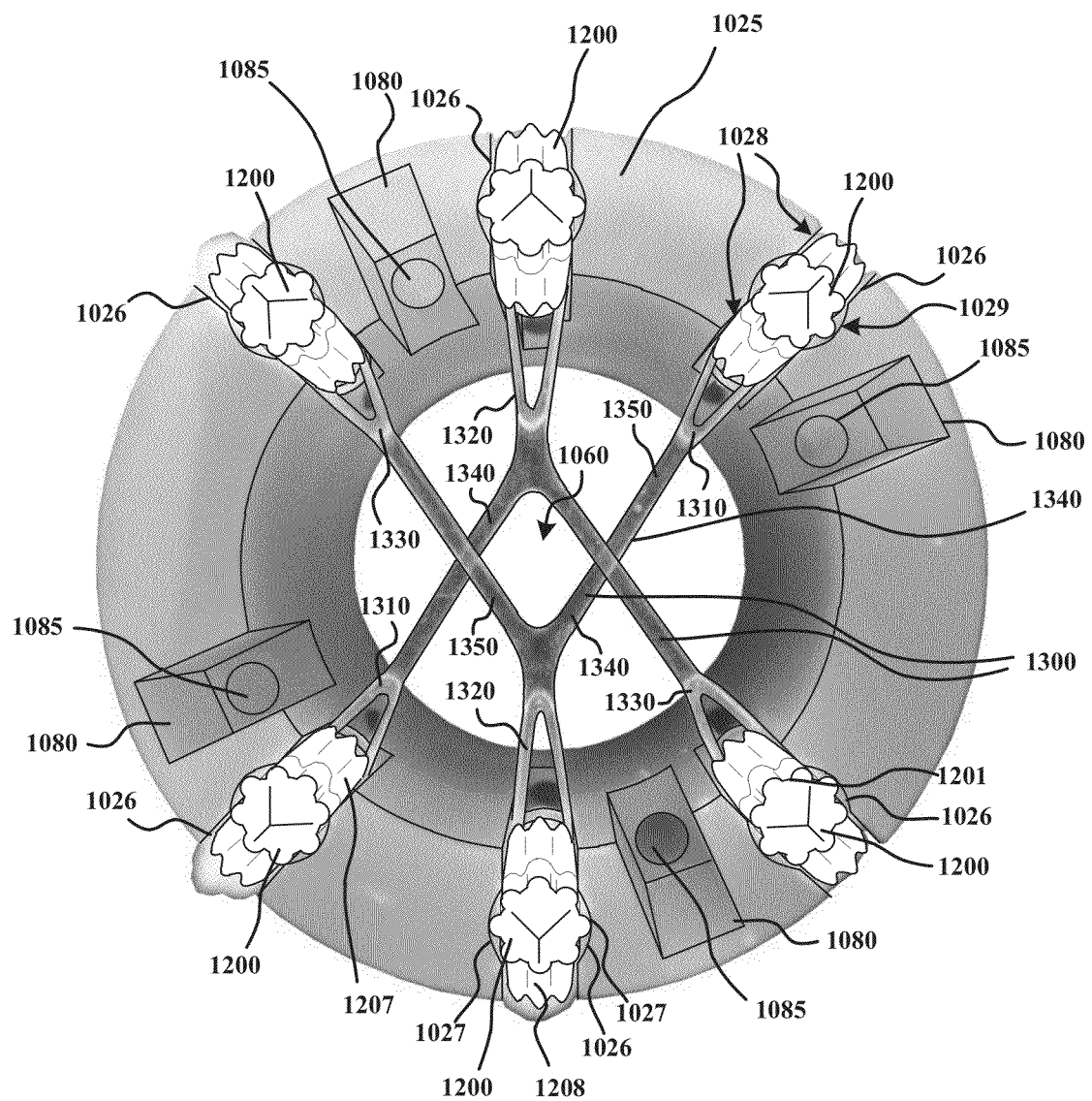
FIG. 16 shows a front perspective view of a distal end portion of the surgical closure device of FIG. 15 with anchors and closure elements.

Referring to FIG. 16, the anchors 1200 are mated with two overlapping closure elements 1300 in the same manner described above. In contrast to the closure elements 300 of the device 5, the closure elements 1300 are not held radially outwardly on the surface of any tube or other structure during driving of the anchors 1200. Rather, the closure elements 1300 form an operational window 1060 via the overlapping V-shaped structure of the closure elements 1300, which is described in greater detail above with regard to closure elements 300, 2300.

Since the centering mechanism 1800, including the guide bore 1810, extends through the operational window 1060 when the guide wire is threaded through the guide bore 1810, it is ensured that the guide wire 1810, as well as any instruments passing over the guide wire 1810, extend through the operation window 1060 after the anchors are driven.

As illustrated in FIG. 16, the tension on the elastomeric closure elements 1300 causes the anchor-receiving portions 1310, 1320, 1330 to stretch and elastically deform. Thus, the apexes of the V-shaped portions have moved closure to each other. Further, the displacement of the vertices causes the anchors 1300 to each have a Y-shaped configuration as illustrated in FIG. 16.

After the anchors are driven into the tissue, the centering mechanism 1800 is separated from the remainder of the device 1005 and distally retracted by sliding along the longitudinal axis x' and along the guide wire away from the surgical site. The centering mechanism 1050 may be removed by the operator by proximally pulling a proximal knob 1057 that projects proximally from the handle 1010.

Upon removal of the guide mechanism 1050, the guide wire exits the guide bore 1810. The proximal free end of the guide wire may then be threaded into a tapered dilator, which may be guided along the guide wire and through the shaft 1020 to the operational window 1060. The dilator may then further progress in order to contact and dilate the tract of tissue through which the guide wire extends. After dilation, the dilator may be proximally retracted and disengaged from the guide wire, at which stage a catheter may be threaded and progressed along the wire, through the shaft 1020 and the operational window 1060. The catheter is further progressed through the dilated tissue opening and into the pericardium. At this stage, the guide wire may be retracted and pericardial fluid allowed to drain through the catheter.

Upon completion of the draining, the catheter may be proximally withdrawn from the surgical site and through the shaft 1020, at which stage there are no surgical components extending through the dilated opening. At this stage, the device 1005 may be proximally retracted from the tissue. The pulling the distal end of the shaft 1020 from the tissue causes disengagement, or release, of the anchors 1200, allowing the closure elements 1300 to pull the anchors 1200 together in the same manner schematically illustrated in FIG. 14, thereby closing the opening in the same manner the opening 1905 is closed in FIG. 14.

Referring to the inset partial view in FIG. 15, the distal end portion 1025 of the shaft 1020 includes six slots 1026 analogous to the slots 26 described above with regard to device 5. In the inset partial view, the anchors 1200 are shown schematically to facilitate illustration of the other components of the device 1005.

Referring to FIG. 16, the slots 1026 of the device 1005 have a cross-sectional shape analogous to the slots 26 of the device 5, including circular bulges corresponding to cylindrical grooves 1027 and dimensioned to allow a small clearance between the diameter of the main body of the anchor 1200. Narrowed portions 1028 extend from opposite sides of the enlarged region 1029 created by the cylindrical grooves 1027. The narrowed portions 1028 are configured to receive the split portions 1207, 1208 of the anchor 1200 but are more narrow than the diameter of the body 1201 of the anchor 1200, thereby ensuring that the anchor 1200 is constrained in the enlarged region 1029 of the cylindrical grooves 1027. Thus, when received in the slots 1026, the anchors 1200 are retained in their axial alignment such that the longitudinal axis xx' is aligned with the longitudinal axis x' of the shaft 1020.

The end portion 1025 is as a separate piece that is attached to the remainder of the shaft 1020. In this regard, the end portion 1025 may be replaced with a like end portion 1025 or an end portion 1025 with a different configuration, e.g., an end portion that holds the anchors in a different pattern. Further, the end portion 1025, together with the anchors and closure elements, may form a cartridge that is used once and discarded, with a new cartridge attached for additional procedures. Moreover, it should be understood that the end portion 1025 may be integrally formed as a single monolithic piece with the remainder of the shaft 1020.

Although the surgical closure device 1005 uses a driving mechanism analogous to the driving mechanism of device 5, including a hammer sleeve and anvil pins (obstructed from view by the shaft 1020 in FIG. 15), the device 1005 includes a different trigger and safety mechanism.

Referring to FIG. 15, the device 1005 includes a trigger 1030 extending below the housing 1010 in the same general direction as the pistol grip 1015 such that when the operator, e.g., a surgeon, grasps the pistol grip 1015, the trigger 1030 is actuatable with the operators fingers, e.g., the index and/or middle fingers, by proximally pulling a gripping portion 1031, which is exposed from the housing 1010, to pivot the trigger 1030 as set forth in greater detail below.

Referring to FIGS. 15 and 17 to 19, the trigger 1030 is pivotable with respect to the handle 1010 about a pivot axis p which corresponds to the longitudinal axis defined by a pivot pin 1040 on which the trigger 1030 is mounted. In particular, the pivot pin 1040 extends within corresponding bore 1032 of the trigger 1030, which is illustrated, e.g., in FIG. 18C. The axial ends of the pivot pin 1040 are mounted in corresponding recesses in the handle 1010.

The trigger 1030 includes a pair of planar faces 1033 that face away from each other in opposite directions along the pivot axis p. The planar faces 1033 extend along in the regions of the trigger around the bore 1032 and extending proximally along a proximal arm 1033.

The proximal arm 1033 extends proximally with respect to the pivot axis p and has a curved upper surface 1034. Extending from each lateral side of the proximal arm are lateral projections 1036, which project outwardly away from respective planar faces 1031 and generally extend parallel to the pivot axis p. The lateral projections 1036 each have a curved upper surface 1037.

A latch member 1045 includes a distally disposed transverse portion 1050 that extends generally along the pivot axis p and transverse with respect to the longitudinal axis x' of the shaft 1020 when the device is assembled. A pair of parallel arms 1055 extends proximally from the transverse portion

1050. Each of the parallel arms 1055 includes a bore 1056 configured to receive the pivot pin 1040 and a pair of opposed faces 1057 configured to receive the trigger 1030 therebetween such that each of the outwardly directed faces 1033 of the trigger 1030 faces a respective one of the inwardly directed faces 1057 of the arms 1055 when the device 1005 is in the assembled state. When the trigger 1030 is received between the arms 1055 of the latch element 1045 in the assembled state of the device 1005, the bores 1056 are concentric with the bore 1032 of the trigger 1030, with the pivot pin 1040 extending through each of the two bores 1056 of the arms 1055 and the bore 1032 of the trigger 1030, thereby provided a mechanism about which the trigger 1030 and the latch element 1045 are pivotable about their common pivot axis p. Thus, the latch member 1045 engages the trigger 1030 at the pivot pin 1040 in a manner analogous to a clevis. Although the trigger 1030 and the latch element 1045 pivot about a single common axis p, it should be understood that the trigger 1030 and the latch element 1045 may pivot about separate axes.

The portions of arms 1055 extending proximally from the pivot axis p include lower surfaces 1058 configured to engage with the upper surface 1035 of the proximal arm 1034 of the trigger 1030. Thus, when the trigger is pulled proximally, the trigger pivots about the pivot axis p in a first rotational direction CW that is clockwise when viewed from the side shown in FIG. 17B.

The transverse portion 1050 of the latch member 1045 also includes a latching projection 1052 that projects upwardly beyond the adjacent structure of the latch member 1045.

Figure 19A:
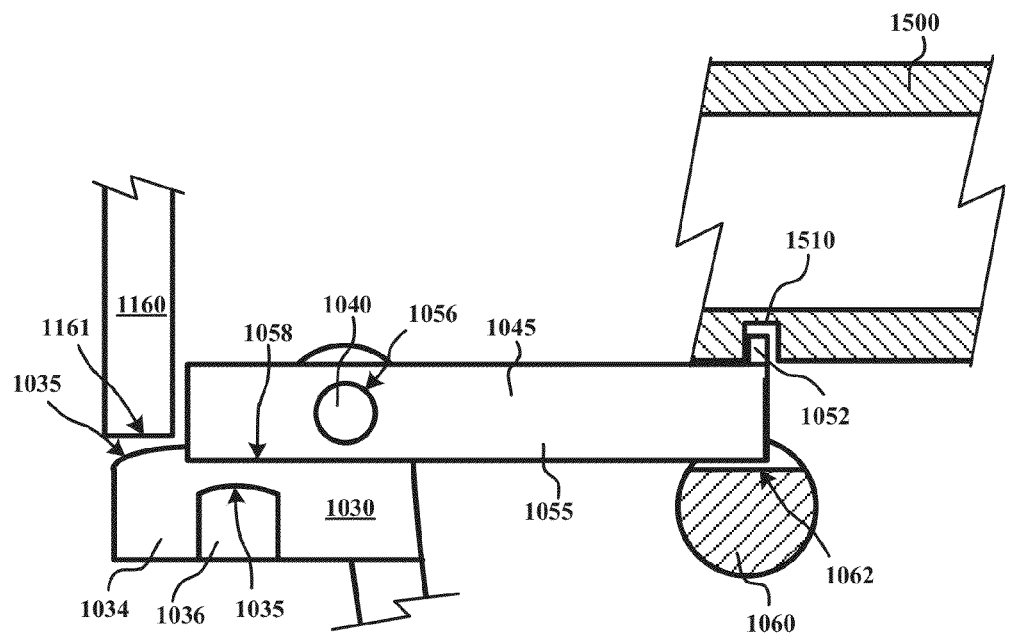
FIG. 19A is a schematic illustration showing the engagement of the trigger bar of the device of FIG. 15 with a hammer sleeve.

Referring to FIG. 19A, a driver in the form of a hammer sleeve 1500 is in its preloaded proximal position and being urged or biased distally by a driving spring 1550 (shown in FIG. 17A) in the same manner as the hammer sleeve 500 of the device 5. The driving spring 1550 is mounted concentrically with respect to the hammer sleeve 1500 and the shaft 1020 and exerts the distally directed force on the hammer sleeve 1500 via a force transfer flange 1560 extending circumferentially around the hammer sleeve 1500. Although the driving springs 550 and 1550 described in connection with devices 5 and 1005 are configured as compression springs, it should be understood that tension springs or other drive mechanisms may be provided.

The hammer sleeve 1500 includes a latching channel 1510 that is configured to receive the latching projection 1052 to thereby restrain the hammer sleeve 1500 by forming a positive stop between the latching projection 1052 and the latching channel 1510. In order to release the hammer sleeve to drive the anchors 1200 in the same manner described above with regard to the device 5, the trigger is pulled distally to pivot the trigger in the first rotational direction CW about the pivot axis p. This pivoted orientation is illustrated in FIG. 19B.

Figure 19B:
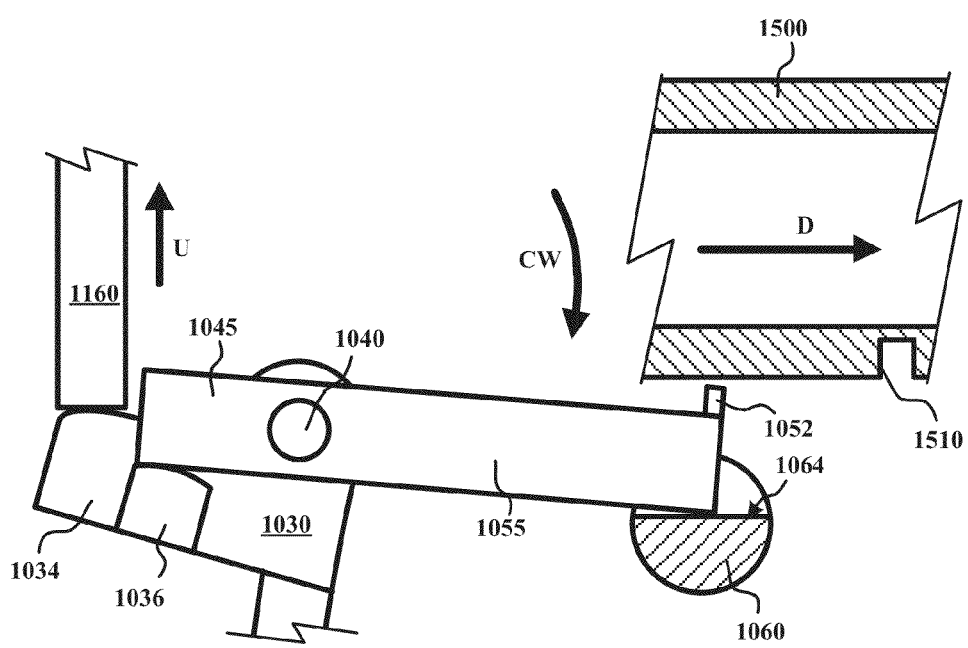
FIG. 19B is a schematic illustration showing the trigger bar of the device of FIG. 15 disengaged with the hammer sleeve.

As illustrated in FIG. 19B, the rotation of the trigger 1030 causes the lateral projections 1036 to contact and push against the lower surface 1058 of the arms 1055, thereby rotating the latch member 1045 into its triggered position, i.e., the position shown in FIG. 19B. In the triggered orientation of the latch member 1045, the rotation of the latch member 1045 has caused the distally located latching projection 1052 to disengage the latching channel 1510 of the hammer sleeve, thereby allowing the hammer sleeve to be driven along the longitudinal axis x' of the shaft 1020 in the distal direction D to drive the anchors 1020.

As illustrated in FIG. 1, there are two safety mechanisms that prevent the release of the hammer sleeve 1500 by the latch member 1045. Both of these safety mechanisms must be simultaneously disengaged, or changed from a locked state to an unlocked state, in order for device to drive the anchors 1200.

The first safety mechanism includes a pressure sensing mechanism including spring-loaded contact elements 1100, illustrated, e.g., in the inset portion of FIG. 15. The contact elements 1100 are configured as rectangular blocks that slide along the longitudinal axis x' of the shaft 1020 between an extended position as illustrated in the inset portion of FIG. 15, wherein the contact elements 1100 extend distance beyond the distal end surface of the shaft 1020, and a proximal position in which the contact elements 1100 are pushed proximally with respect to the shaft 1020, e.g., until the contact elements 1100 are flush with the distal ends of the shaft 1020. The safety release mechanism may include a plurality of spring-loaded members, each spring-loaded member independently movable between an engagement position and a disengagement position, the safety release mechanism adapted to prevent the driver from driving the anchors unless all of the spring-loaded members are in the engagement position.

Each contact element 1100 is axially slidable within a respective correspondingly dimensioned slot 1080, illustrated, e.g., in FIG. 16. Although the illustrated example includes four rectangular contact elements that are evenly spaced at approximately 90-degree increments about the longitudinal axis x' of the shaft 1020, it should be understood than any appropriate number (including one) of contact elements 1100 having any suitable geometry and disposed at any suitable location(s) may be provided.

Figure 17A:
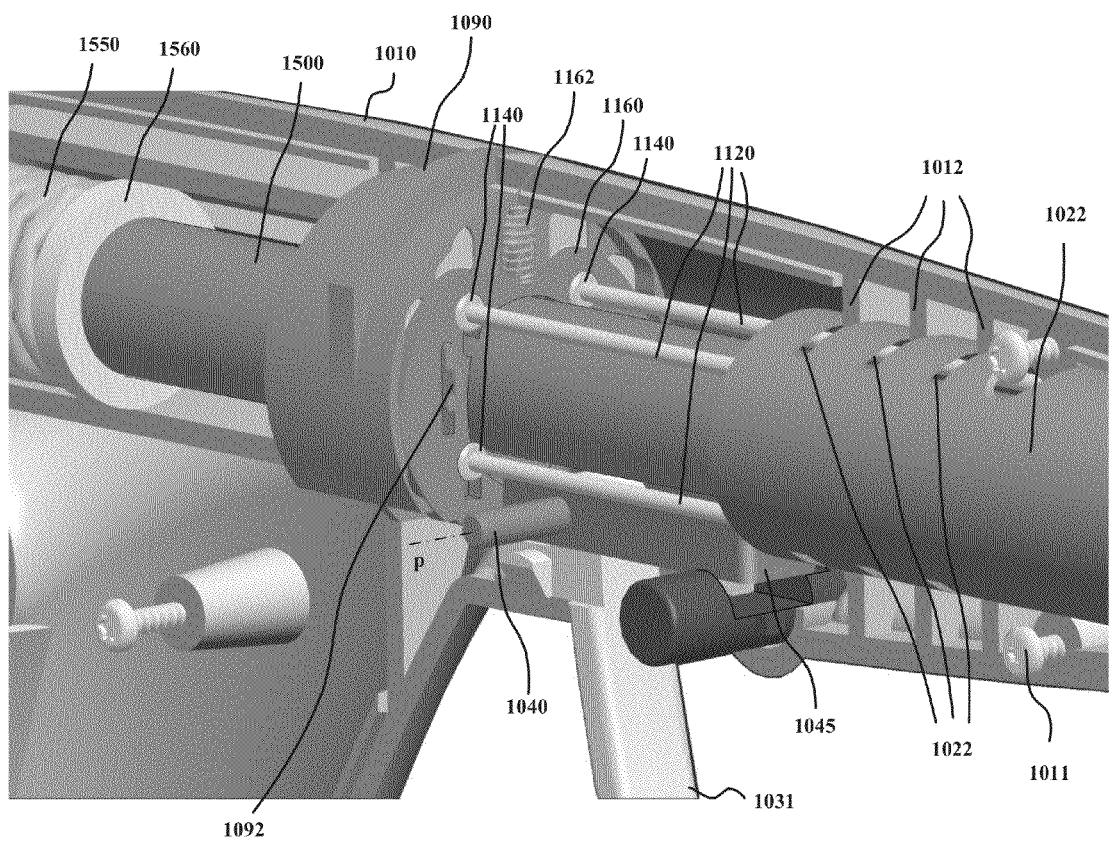
FIG. 17A is a partial view of a subassembly of the device of FIG. 15.
Figure 17B:
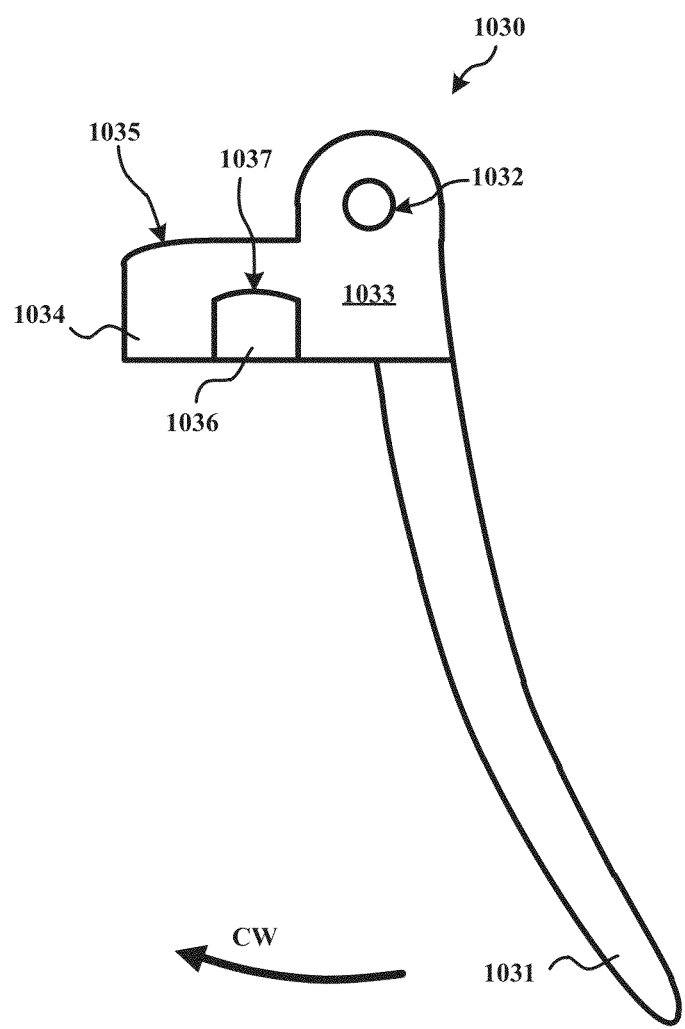
FIG. 17B is a side view of the trigger of the device of FIG. 15.
Figure 17C:
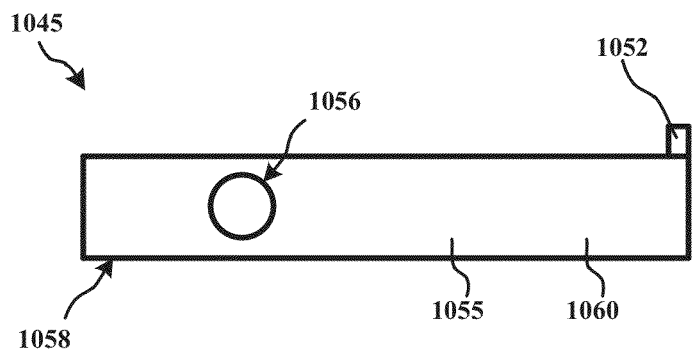
FIG. 17C is a top view of the trigger of the device of FIG. 15.
Figure 17D:
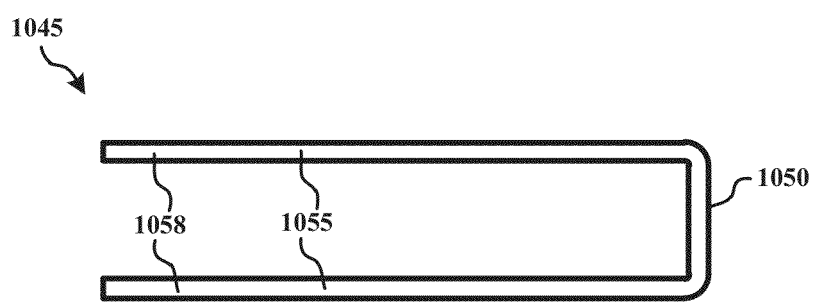
FIG. 17D is a bottom view of the trigger of the device of FIG. 15.

Each contact element 1100 is supported on a respective pressure transfer shaft 1120 that extends and is axially slidable within a respective bore 1085 that extends parallel to the longitudinal axis x' of the shaft 1020. Each pressure transfer shaft 1120 is proximally coupled to a key member 1140, which as illustrated in FIG. 17A, extends into and engages a key plate 1160. One or more springs exerts a spring force on the key members 1140 to urge or bias the contact elements 1100 toward their distally extended positions.

When the distal end of the shaft 1020 is pressed against a tissue through which the anchors 1200 are desired to be driven, the tissue exerts a proximally directed pressure on the contact elements 1100, which are initially in their distally extended positions due to the spring loading. The contact elements are pushed proximally with respect to the shaft 1020 when the pressure exerted by the tissue exceeds the bias or urging force of the spring(s). This proximal movement within each slot 1080 is mechanically transferred via the respective pressure transfer shaft 1120 to the key element 1140, thereby moving the key member proximally beyond the key plate 1160. In this regard, the there is a substantially 1:1 relationship between the axial movement of each contact element 1100 and the respective key member 1140. It should be understood, however, that the device may be configured to provide a relationship between axial movement of the key member 1140 and the axial movement of the respective contact element 1100 that is other than 1:1. Further, although the example device 1005 utilizes sliding shafts 1120 to mechanically couple and transfer force from the contact elements 1100 to the respective key members 1140, the contact elements may be mechanically coupled to the key members 1140 by other mechanisms, e.g., hydraulic and/or pneumatic systems.

The key plate 1160 is slidable within the handle 1010 along an axis transverse to the longitudinal axis x' of the shaft 1020 and the pivot axis p defined by the pivot pin 1040. In this regard, the key plate 1160 is slidable between a first position, illustrated in FIGS. 17A, 18A, and 19A, and a second position, illustrated in FIGS. 18B and 19A. The movement of the key plate 1160 between the first and second positions is along a path that is substantially within a plane perpendicular to the pivot axis p. Referring the FIG. 19B, the key plate 1160 moves from the first position to the second position by moving in the direction U. Although the path the key plate 1160 travels between the first and second positions is linear, it should be appreciated that the path may be non-linear, e.g., curved. Further, a plane that includes the pivot axis p and intersects a bottom surface 1161 of the key plate 1160 rotates in the first rotational direction CW when the key plate 1160 moves from the first position to the second position. Likewise, the plane rotates in a second rotational direction opposite the first direction CW when the key plate moves from the second position to the first position.

The key plate 1160 is slidably supported by a proximal support block 1090 that is fixedly mounted in the handle 1010 of the device 1005. In the illustrated example, the key plate 1140 is supported by a pair of parallel guide ribs 1092 of the support block 1090 so that the key plate 1160 is slidable between the first and second positions. The support block 1090 also supports each of the key members 1140 so that each of the key members 1160 are slidable along the longitudinal axes f, g, h, i of the respective shaft 1140 to which the key member 1140 is attached. Thus, the key members 1140 are permitted to slide axially along axes f, g, h, i, but are constrained from moving with respect to the handle 1010, shaft 1020, and other fixed components of the housing of the device 1005.

The geometry of the key plate 1160 is selected such that the key plate 1160 is prevented from moving to the second position if any one of the key members 1140 is still engaged with the plate, which would indicate that one of the contact elements 1100 at the distal end of the shaft 1020 is not fully proximally depressed.

The geometry of the key plate 1160 is such that each of the pressure transfer shafts are allowed to pass through the key plate 1160 when the key plate is either of the first and second positions. However, the geometry of the key plate 1160 does not allow any of the key members 1140 to extend axially into any recess defined by the key plate 1160 when the key plate 1160 is in the second position. In the illustrated example, this is achieved due to the fact that each key member 1140 has a diameter, when viewed along a line parallel to the direction of movement of the plate 1160, that is greater than a diameter of the respective pressure transfer shaft 1120 to which it is coupled.

Figure 18A:
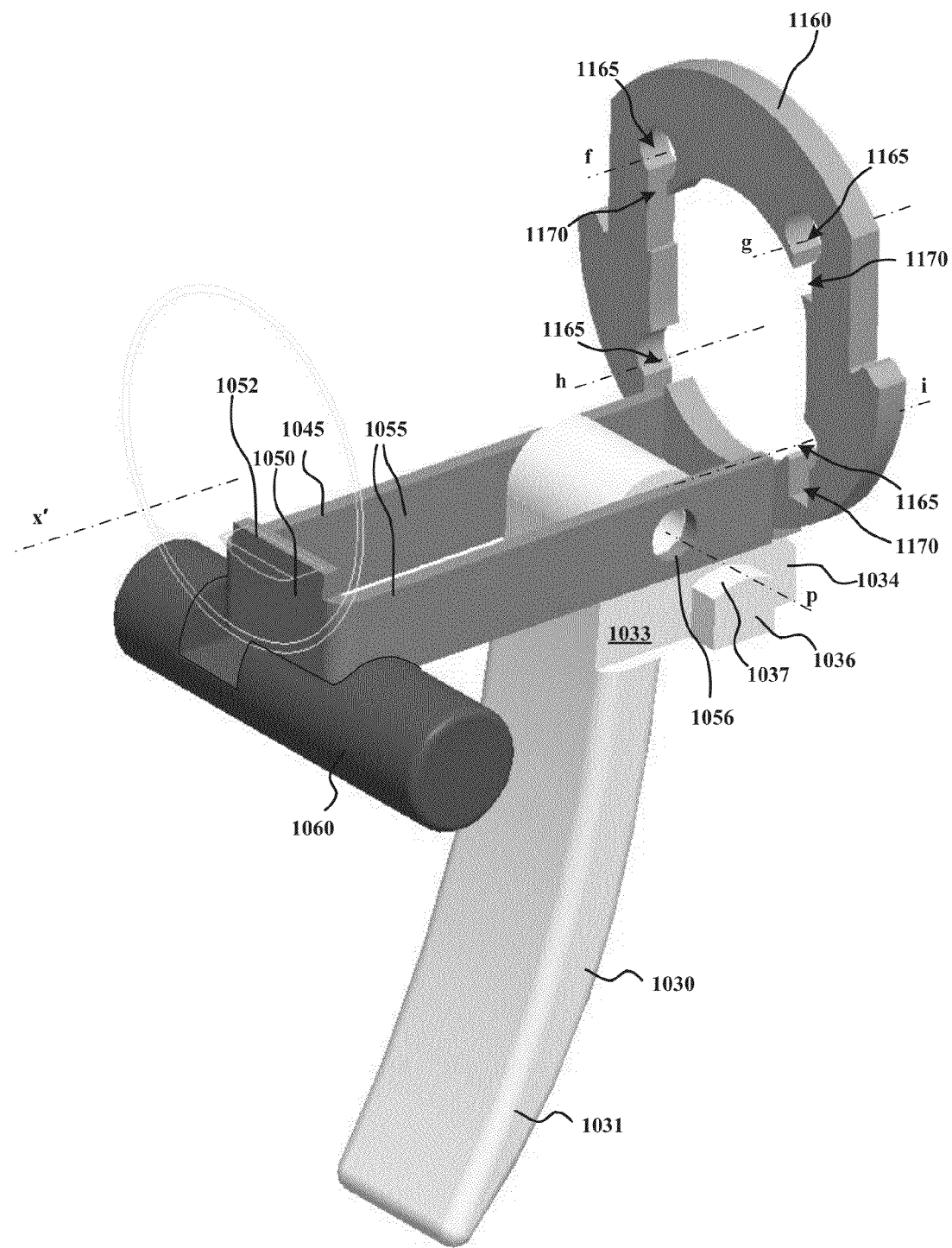
FIG. 18A is a partial view of a trigger subassembly of the device of FIG. 15 with the trigger in an initial state.
Figure 18B:
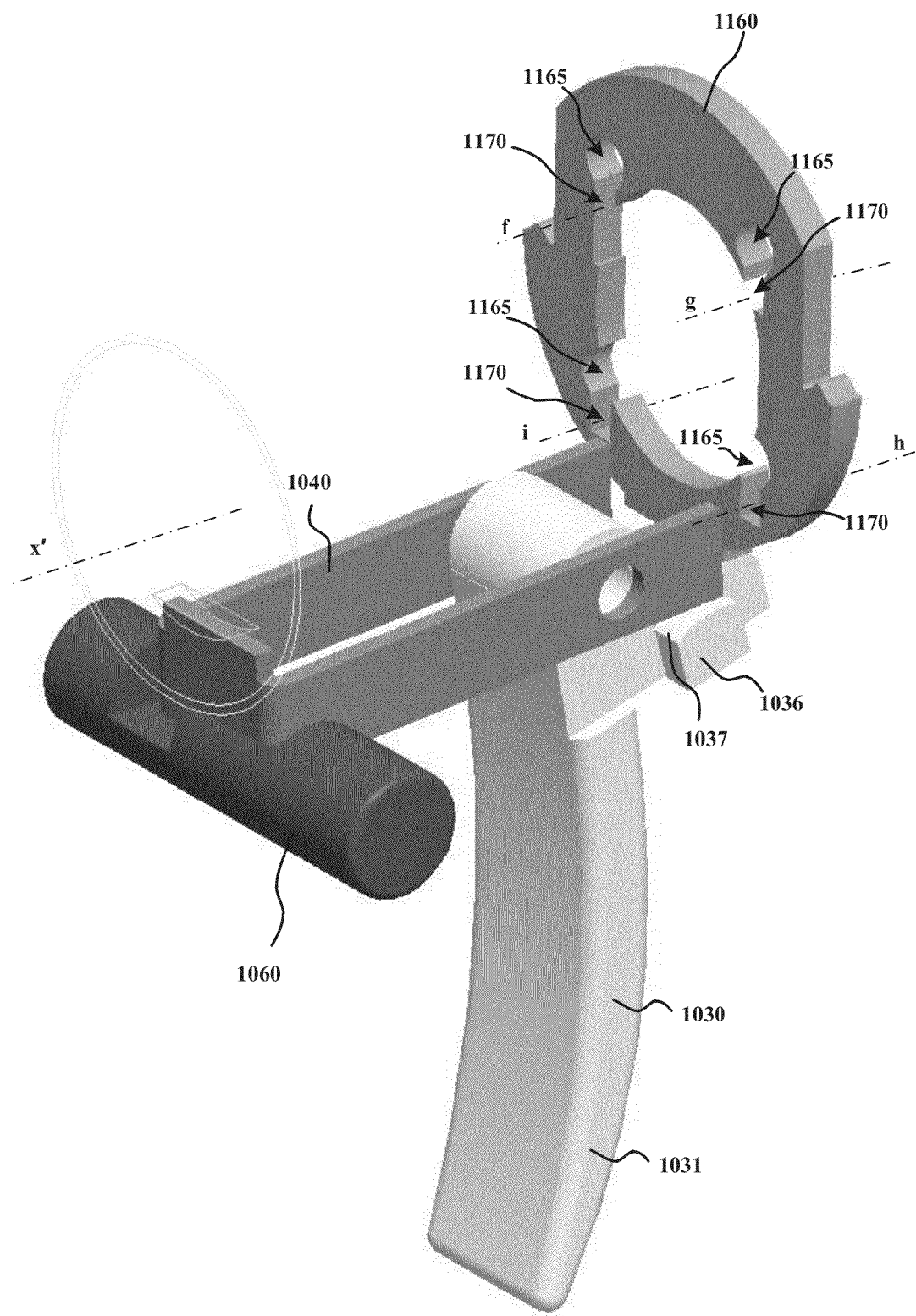
FIG. 18B is a partial view of the trigger subassembly of FIG. 18 with the trigger depressed.

Referring to FIGS. 18A to 18E, the key plate 1160 has a complex cutout geometry including enlarged regions 1165 configured to axially receive respective key members 1140. Referring to FIG. 18A, when the key plate 1160 is in the first position, the clearance between the structure of the key plate 1160 and the respective enlarged regions 1165 where the longitudinal axes f, g, h, and i of the four respective pressure transfer shafts 1120 pass through the key plate 1160 is sufficient to axially receive the key member 1140. Referring to FIG. 18B, when the key plate 1160 is in the second position, the clearance between the structure of the key plate 1160 and the respective regions 1170 where the longitudinal axes of the pressure transfer shafts 1120 pass through the key plate 1160 is insufficient to axially receive the key member 1140, but great enough to allow the pressure transfer shafts 1120 to pass through.

Figure 18C:
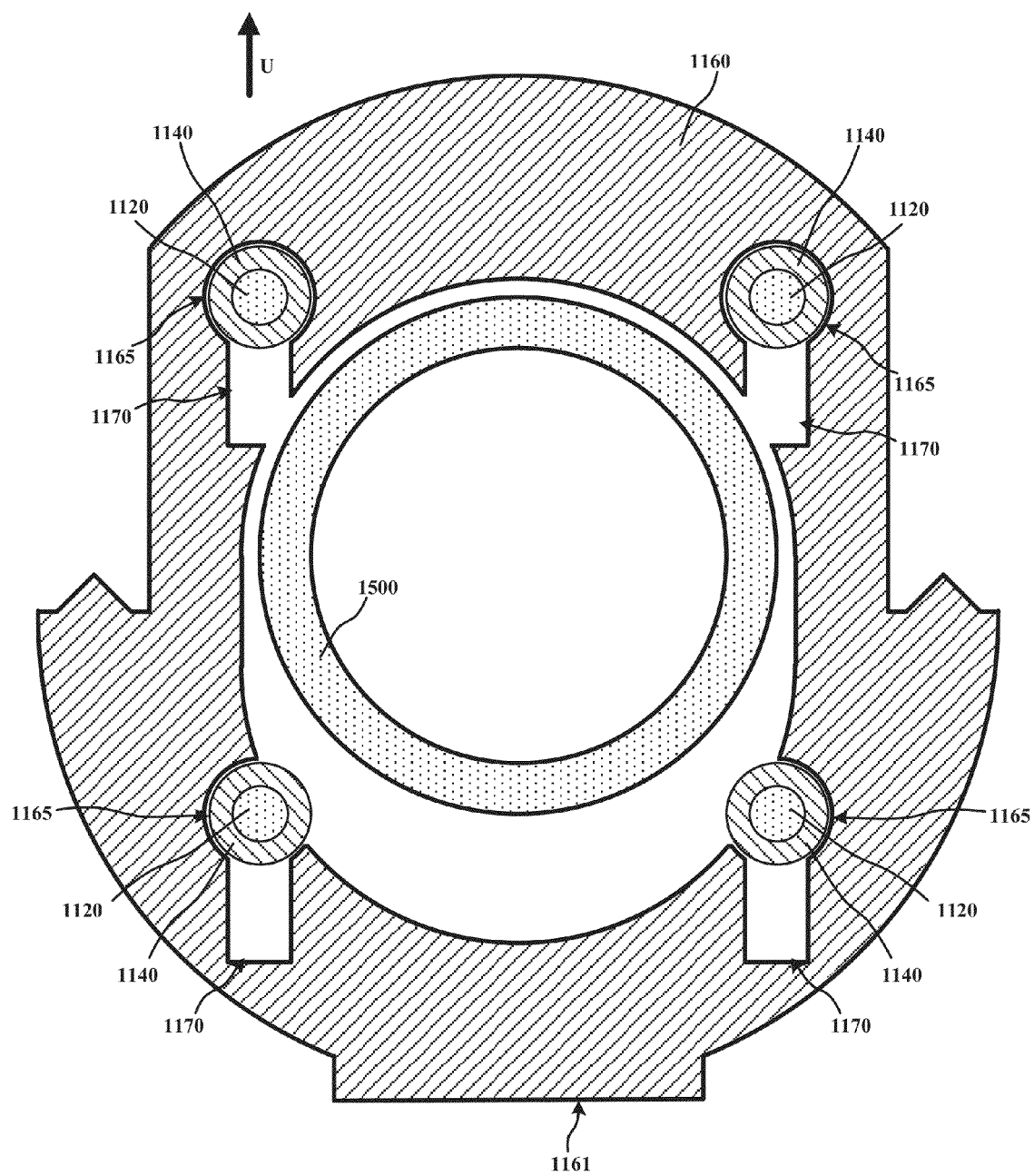
FIG. 18C is a front cross-sectional view of a subassembly of the device of FIG. 15 showing the key plate in an engaged state and in a first position.
Figure 18D:
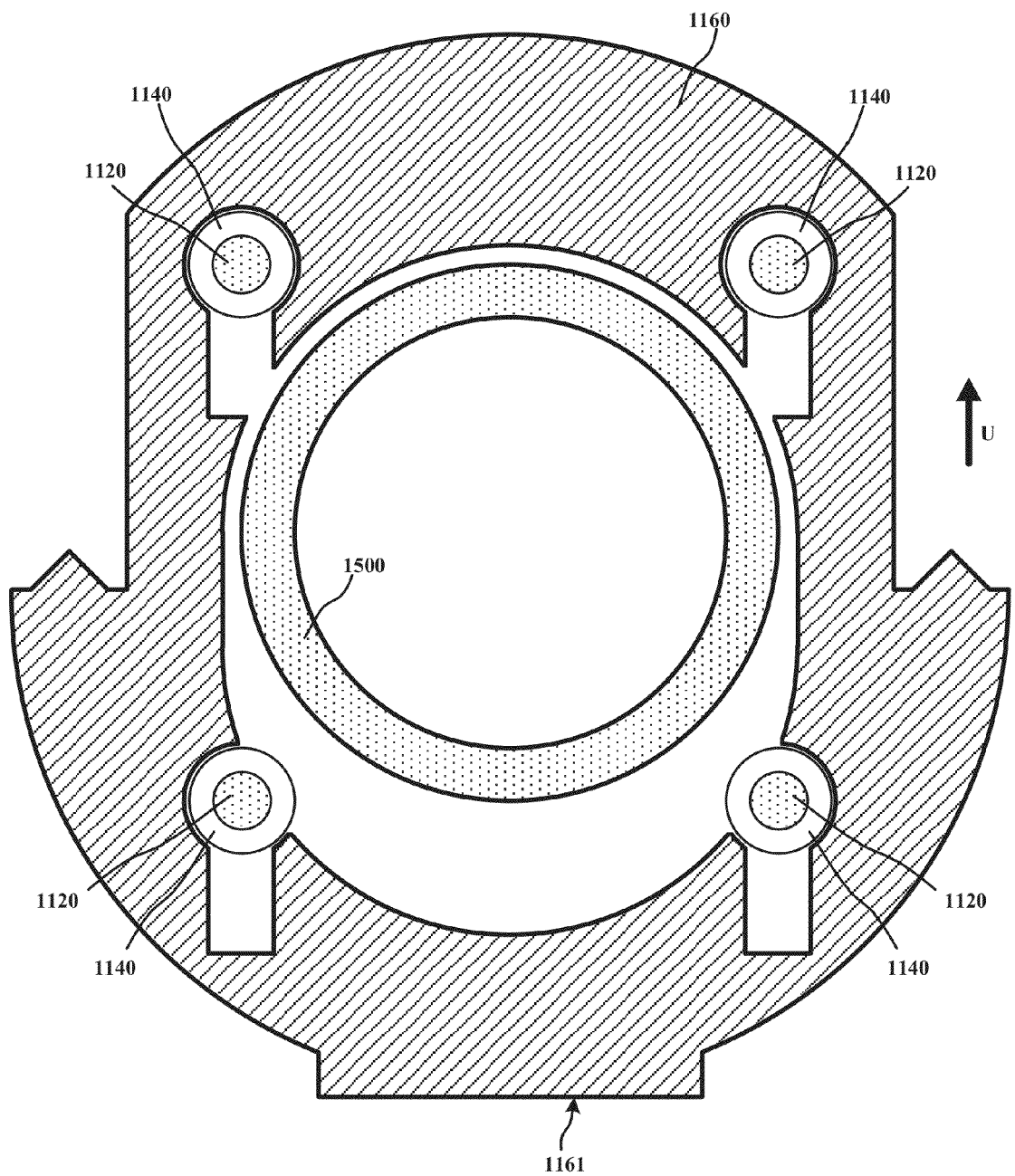
FIG. 18D is a front cross-sectional view of the subassembly of FIG. 18C showing the key plate in a disengaged state and in the first position.
Figure 18E:
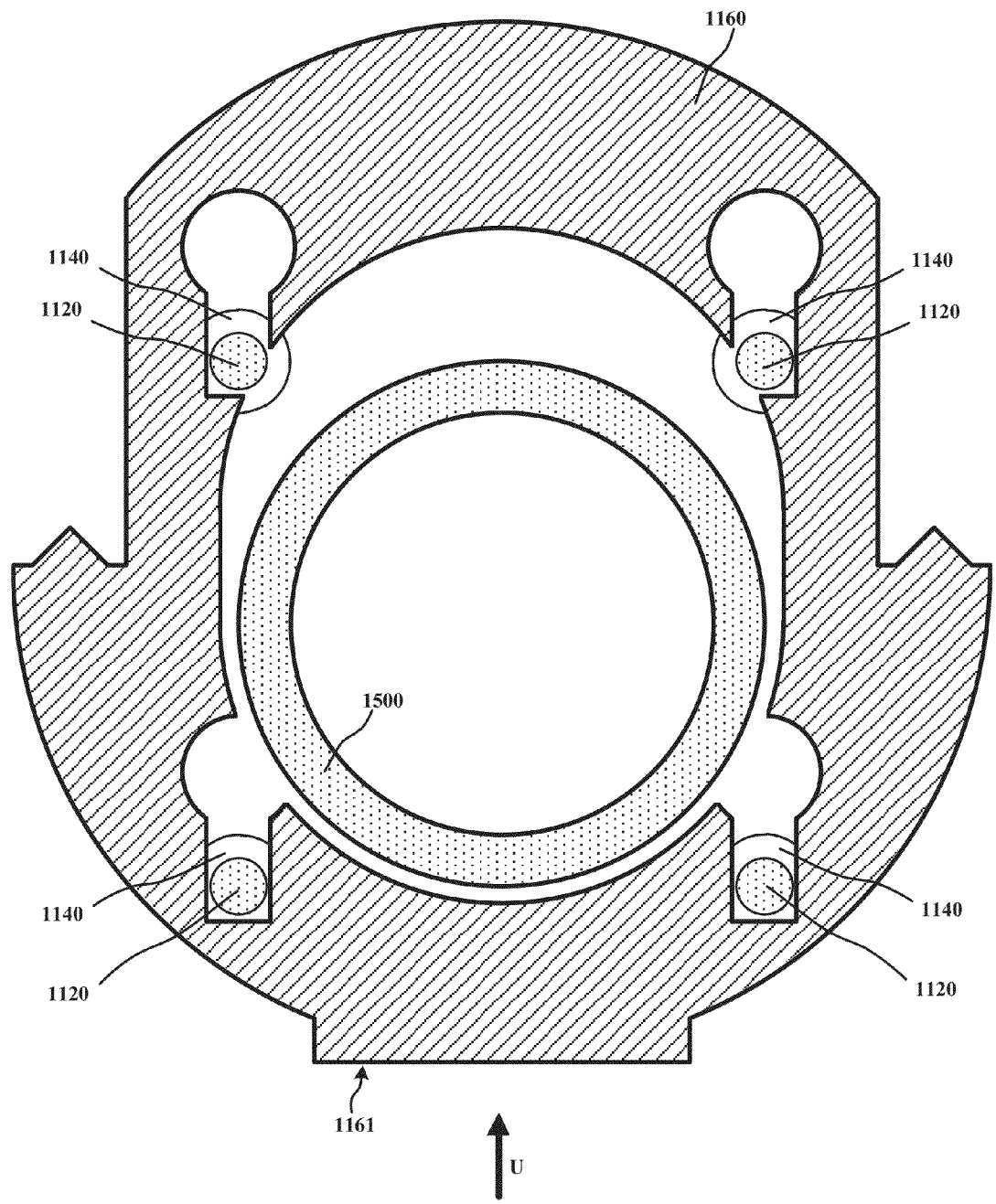
FIG. 18E is a front cross-sectional view of the subassembly of FIG. 18C showing the key plate in a disengaged state and in a second position.

As illustrated in FIG. 18C the geometry of each key member 1140 is received in a closely fitting corresponding recess of the key plate 1160 such that the key plate 1160 is not able to move in the direction U from the first position (illustrated, e.g., in FIGS. 18C and 18D) to the second position (illustrated in FIG. 18E). Referring to FIG. 18D, all four of the key members 1140 have been proximally depressed via the proximal depression of the corresponding contact elements 1100 at the distal end of the shaft 1020, thereby resulting in the key plate being in a disengaged state with respect to the key members 1140. As illustrated in FIG. 18D, the key members 1140 are have proximally cleared the structure of the key plate 1160 while the key plate 1160 is in the first position. At this stage, the regions 1170 of the key plate 1140 are able to receive the shafts 1120, which have reduced diameters with respect to the respective key members 1140 to which the shafts 1120 are attached. Thus, the key plate 1140 is in an unlocked state since it is able to be moved in the direction U from the first position illustrated in FIG. 18D to the second position illustrated in FIG. 18E. As previously indicated, this movement is achieved by contact and application of force between the upper surface 1035 of the proximal extension 1034 of the trigger 1030

Since the key members 1140 are radially constrained in the handle 1010, the key plate 1160 is prevented from moving to the second position when any one or more of the key members 1160 are extended into the cutout geometry of the key plate 1160. Thus, the first safety mechanism is in a locked state when any one of the contact elements 1100 is not fully depressed, leading to engagement between at least one of the key members 1140 and the key plate 1160.

Referring again to FIG. 19A, since the key plate is not allowed to move from the illustrated first position in the locked state, contact between the upper surface 1035 of the proximal arm 1034 of the trigger 1030 and the lower surface 1161 as the trigger 1030 would form a positive stop to prevent the trigger 1030 from adequately rotating to disengage the latch member 1045 from the hammer sleeve 1500. Thus, all four contact elements 1100 must be depressed in order for the device 1005 to drive the anchors 1200. This safety mechanism is advantageous because it requires that the distal end of the shaft 1020 be properly seated against the tissue before driving the anchors 1200, thereby reducing the possibility of inadvertent or improper driving of the anchors 1200.

As illustrated in FIG. 17A, the key plate 1160 is urged toward the first position by a spring 1162. Since the operator may need to reposition the distal end of the shaft 1020 before driving the anchors 1200, the spring urging or biasing of the contact elements 1100 toward the first position ensures that the contact elements 1100 will spring back to their extending positions. For example, the operator may press the distal end of the shaft 1020 against a first portion of tissue such that all four of the contact elements 1100 are sufficiently depressed, thereby causing all four of the key members 1140 to move proximally from the key plate 1160. At this stage, the first safety mechanism is in a disengaged state, in order to allow firing if the operator pulls the trigger 1030. Thus, the key plate 1160 is slidable between the first and second positions. If there were no urging of the key plate 1160 toward the first position, the key plate 1160 could inadvertently slide to a position (e.g., the second position or a position between the first and second positions) that would prevent the key members 1140 from re-engaging the key plate 1160. Thus, even if the operator pulls the distal end of the shaft 1020 away from the first portion of tissue, e.g., to reposition the device 1005, first safety mechanism would remain in the disengaged state and the contact elements 1100 would not be returned to their distally extended positions via the bias spring force. Thus, the first safety mechanism would not be effective at this stage. Since the spring 1162 acts to urge the key plate 1160 toward its first position, it serves to ensure that the distal end of the shaft 1020 may be repositioned multiple times without rendering the first safety mechanism ineffective.

The housing 1010 includes a window 1013 that provides a visual indication to the operator regarding the state of the contact elements 1100. For example, there may be four discrete indicators that corresponding to respective contact elements 1100. Thus, the operator would be able to see that less than all of the four contact elements 1100 are depressed and would therefore know to continue maneuvering the device until all four contact elements 1100 are depressed. Further, the indicators may allow the operator to know which specific contact element 100 is not depressed, so that that the operator may maneuver the device 1005 accordingly.

Although the pressure sensing of device 1005 is purely mechanical, it should be understood that other pressure sensing arrangements may be provided. For example, electronic pressure sensors may be provided.

Figure 19C:
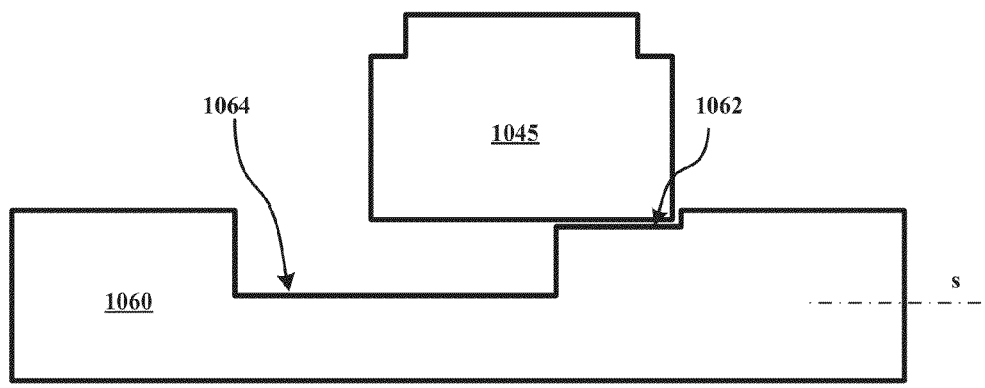
FIG. 19C is a schematic front view of the latch member and safety switch of the device of FIG. 15 with the safety switch in an engaged state.
Figure 19D:
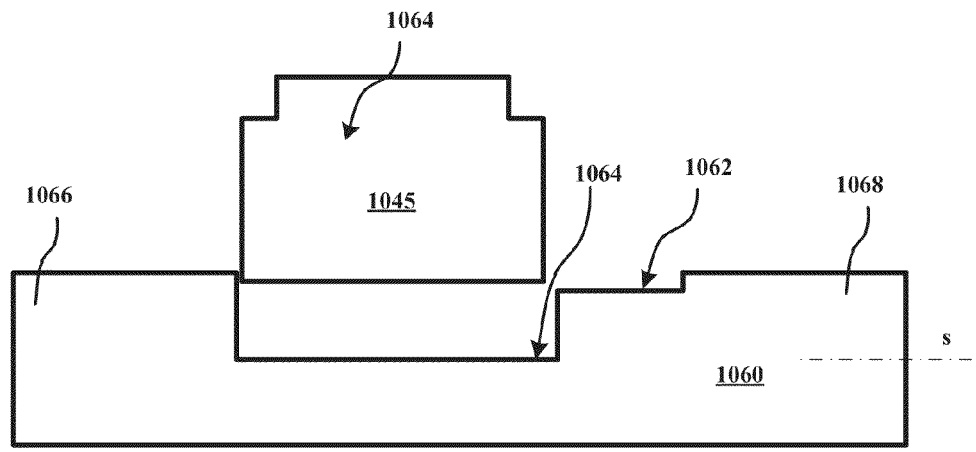
FIG. 19D is a schematic front view of the latch member and safety switch of the device of FIG. 15 with the safety switch in a disengaged state.
Figure 20A:
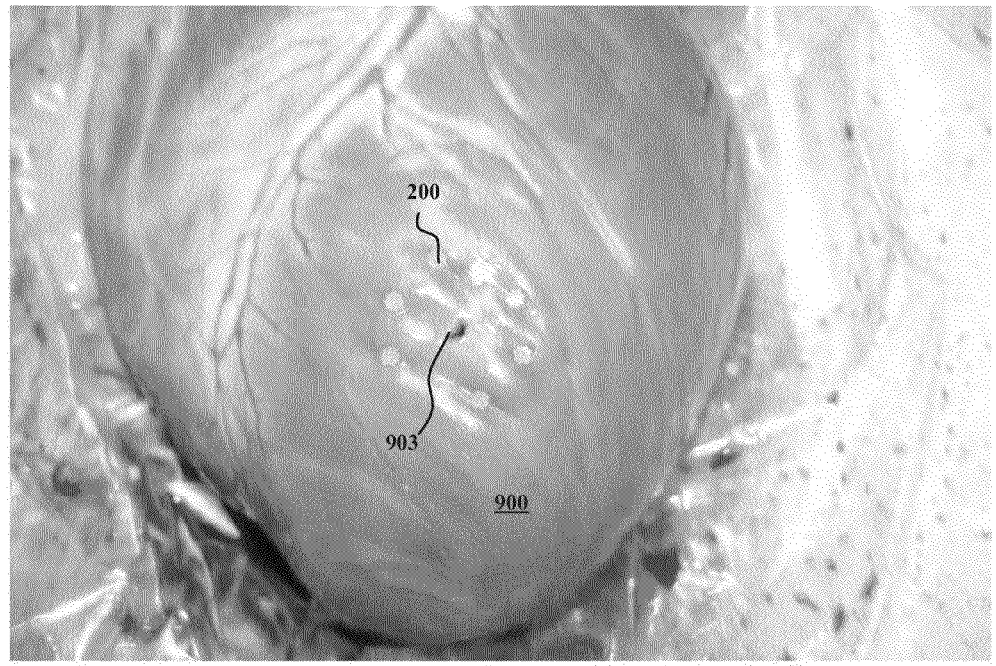
FIG. 20A shows the anchors driven into a tissue without closure elements.
Figure 20B:
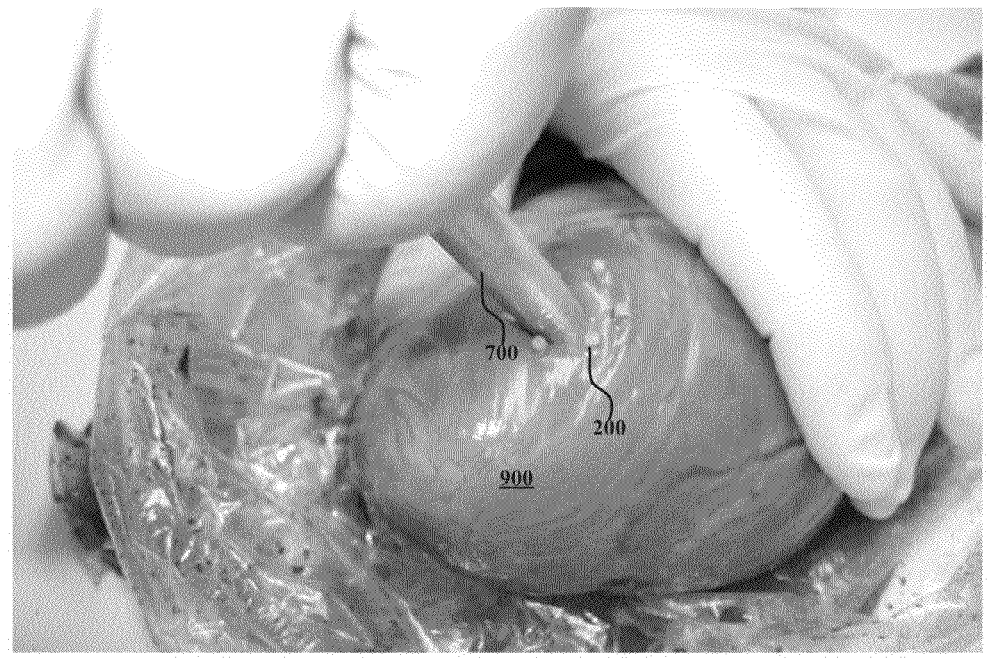
FIG. 20B shows the tissue of FIG. 20A punctured at a location within the periphery defined by the anchors.
Figure 20C:
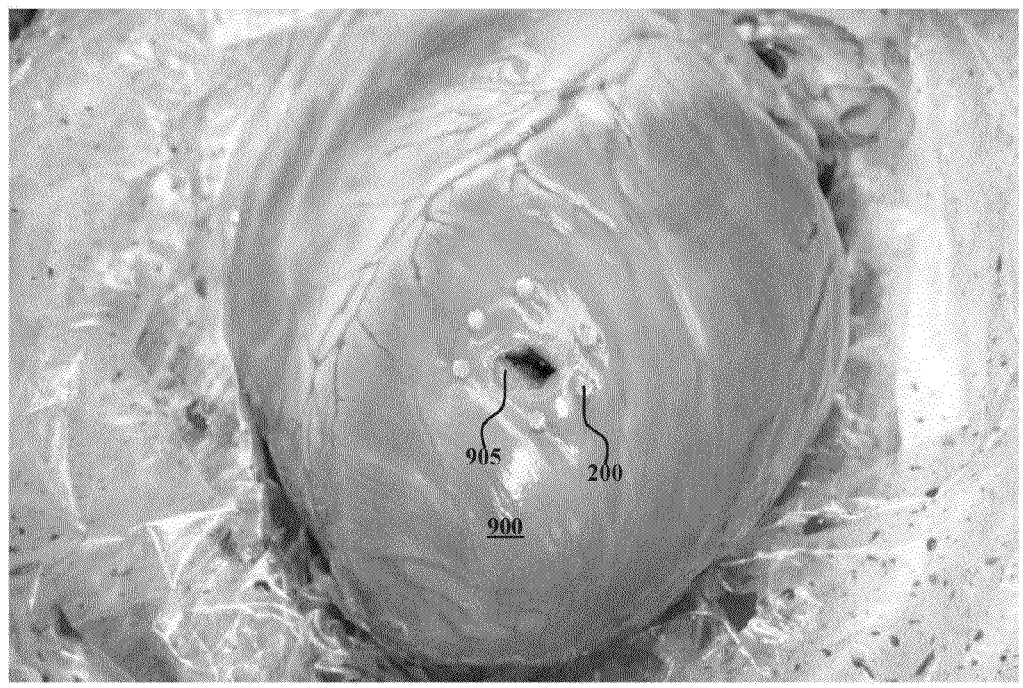
FIG. 20C shows the anchors disposed around the puncture formed in FIG. 20B.
Figure 20D:
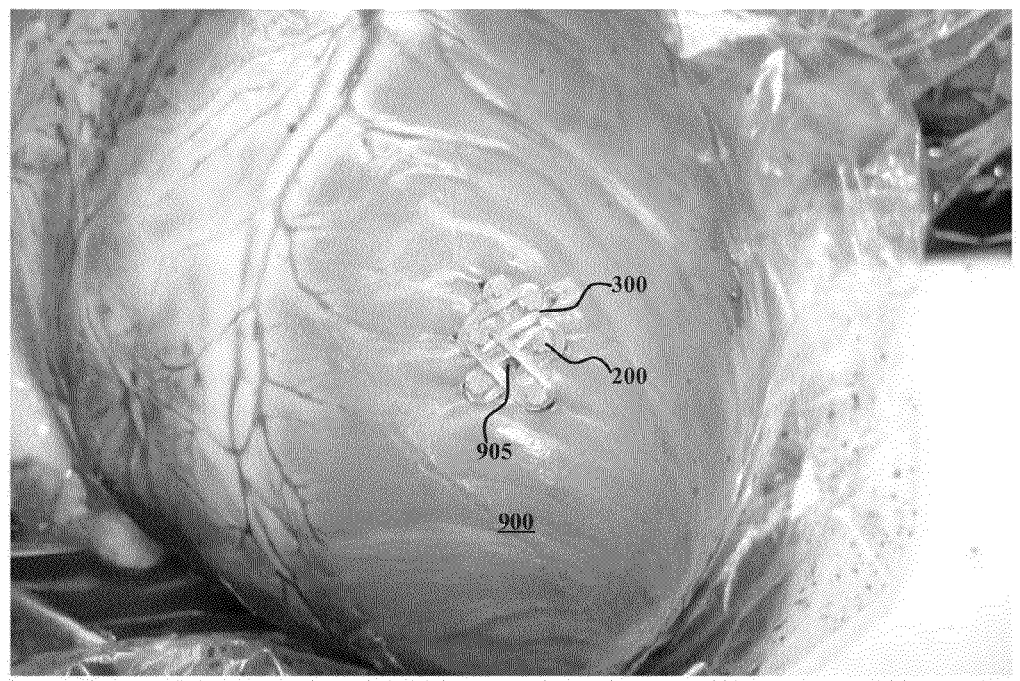
FIG. 20D shows the puncture of FIGS. 20B and 20C closed by the anchors and closure elements.
Figure 20E:
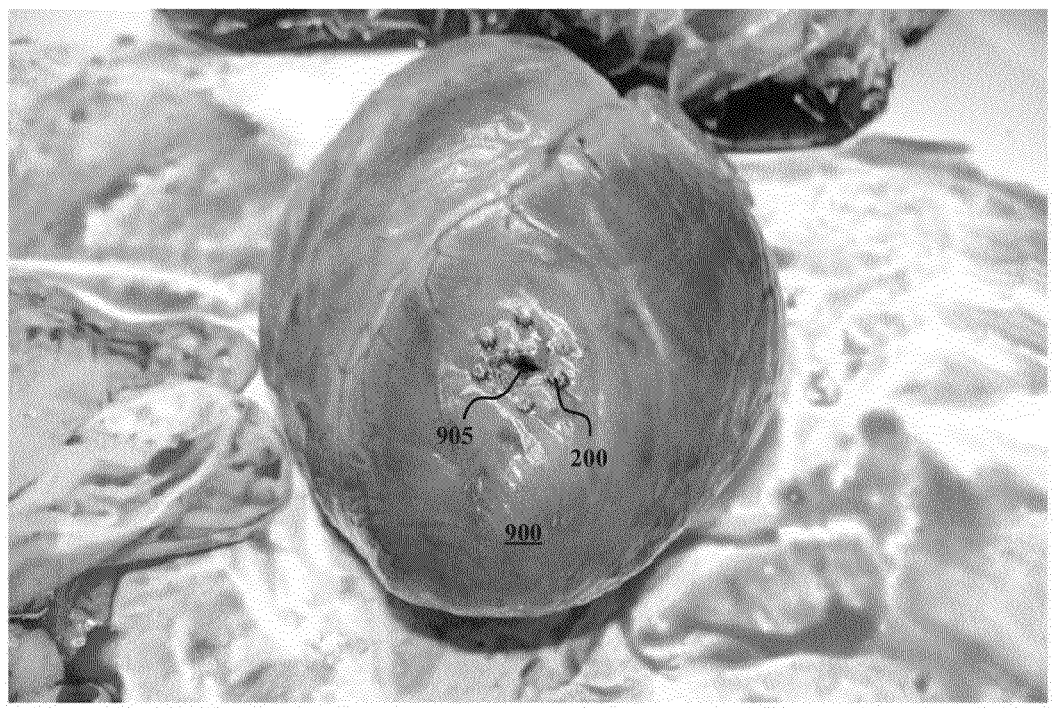
FIG. 20E shows the anchors surrounding the punctured tissue.

The second safety mechanism includes the safety switch 1060. As illustrated in FIGS. 19A and 19C, the safety switch 1060 is in a first position in which a first surface 1062 of the safety switch 1060 forms a positive stop against the bottom surface of the latch member 1045 to prevent the latch member 1045 from rotating about the pivot axis p into the disengaged position illustrated, e.g., in FIG. 19B.

The safety switch 1060 is slidably mounted within a corresponding bore of the handle 1010. The safety switch 1060 is slidable about its longitudinal axis s between the first position with respect to the latch member 1045 and the second position with respect to the latch member 1045, illustrated in FIGS. 19B and 19D. In this regard, a first axial end 1066 is exposed from a first side of the housing 1010 and an opposite axial end 1068 is exposed from a second side of the housing 1010. The operator may move the safety switch from the first position to the second position by pressing the first axial end 1066 along the axis s. Likewise, the operator may move the safety switch from the second position to the first position by pressing the second axial end 1068 along the axis s.

In the second position, the first surface 1062 has moved along the axis s to a position that does not impede the rotation of the latch member 1045. Thus, the latch member 1045 is freed to rotate to the second position to thereby release the hammer sleeve 1500 and drive the anchors 1200. Accordingly, the second safety mechanism is engaged when the safety switch is in the first position and disengaged when the safety switch is in the second position.

A second surface 1064 forms a positive stop to prevent the latch member 1045 from rotating in the direction CW beyond the second position.

As indicated above, both safety mechanisms must be disengaged in order to drive the anchors 1200 from the device 1005. The first safety mechanism ensures that the distal end of the shaft 1020 is properly seated against the tissue and the second safety mechanism prevents unintended firing due to inadvertent pulling of the trigger 1030. In this regard, the operator may wish to keep the second safety mechanism engaged until satisfied with the placement of the distal end of the shaft 1020.

Although the first and second safety mechanisms in the illustrated examples are entirely mechanical, it should be understood that other mechanisms may be provided. For example, electronic elements may be incorporated into the system and/or specific force or pressure values at the locations of the contact elements may be interpreted by a processor and a decision made, e.g., according to an algorithm, whether or not to allow driving of the anchors 1200.

Referring to FIG. 17A the handle 1010 is formed as two corresponding injection molded halves, one of which is illustrated in FIG. 17A. Each half of the handle 1010 includes various structures configured to receive and support other components within the handle 1010. For example, a plurality of support ribs 1012 mate with a corresponding pair of respective support slots 1012 in the shaft 1020 to secure the shaft 1020 to the handle 1010 when the device is assembled. In the assembled state, the first and second halves are connected by anchors 1011, which are screws in the illustrated example. Although an injection molded handle with two joined halves is provided, it should be appreciated that the handle 1010 may be formed in any appropriate manner.

The closure elements 300, 1300, 2300 disclosed herein may be elastomeric, e.g., silicon. It should be understood, however, that the closure elements 300, 1300, 2300 may be formed of any appropriate material, e.g., a bio-absorbable material. Further, where the anchors 200, 1200 are also formed of bio-absorbable material, the entire self-acting closure assembly including anchors 200 and/or 1200 as well as closure elements 300, 1300, and/or 1400 (which is typically left in the patient after completion of the procedure) may be absorbable into the patient's body. Although a plurality of elastomeric closure elements 300, 1300, 2300 are described in connection with the exemplary embodiments, it should be a single continuous closure element may be provided (e.g., a single monolithic piece that extends among the various anchors 200, 1200). Further, as an alternative or in addition to the one or more elastomeric closure elements, any other urging mechanism, e.g., springs, may be provided as a closure element. Further, it should be understood that the pattern according to which the anchors 200, 1200 and closure elements 300, 1300, 2300 are oriented may vary from the exemplary embodiments described herein.

Although the described use of the example device 5 includes driving of the anchors 200, 1200 prior to forming a surgical access aperture, it should be understood that the anchors 200, 1200 may be driven after forming the aperture. Similarly, it is feasible to drive the anchors 200, 1200 from the device 1005 prior to dilating the hole. However, driving the anchors after forming the aperture or dilating the hole may be less advantageous because the formation of the aperture in the former procedure and the dilation in the latter presses tissue away from the hole and any subsequently driven anchors would therefore be at a location closer to the aperture when the tissue is in a relaxed state. Thus, the amount of tissue between the anchors 200, 1200 would be less, likely resulting in less compressive force being exerted to the tissue in comparison to anchors driven prior to forming the surgical access aperture.

Further, it should be understood that the closure devices 5, 1005 may be provided in connection with any appropriate surgical device, e.g., a flexible thoracoscopic shaft. Moreover, any appropriate driving mechanism for driving the anchors 200 may be provided.

Although the closure elements 300, 1300, 2300 are each formed as a single monolithic piece, it should be understood that any closure element described herein may be comprised of multiple component pieces.

Moreover, although the examples described herein are describes as firing a plurality of anchors 200, 1200 that are each identical to each other, it should be understood that a driven set of anchors may include one or more anchors that differ from the other anchors of the set. For example, situations with non-uniform tissue properties and/or dimensions may be addressed by firing, e.g., simultaneously, different types of anchors at different locations. In this regard, the device 5, 1005 may be adapted to receive different types of anchors in the same slot and/or have interchangeable housing portions to receive the various anchors.

Further, the anchors 200, 1200 may include any of the features of the fasteners or other analogous implants disclosed in U.S. Provisional Patent Application Ser. No. 61/296,868, filed on Jan. 20, 2010 and in U.S. Patent Application Ser. No. 13/010,766, filed on Jan. 20, 2011, and may be driven using any mechanism disclosed therein.

Further, any of the implantable elements described herein, e.g., anchors 200, 1200 and/or closure elements 300, 1300, 2300 may be formed wholly or partly of a material absorbable into the patient's body, or of a non-absorbable material, depending on, e.g., the specific application. For example, these elements may be formed of polyglycolic acid (PGA), or a PGA copolymer. These elements may also, or alternatively, be formed of copolymers of polyester and/or nylon and/or other polymer(s). Moreover, these elements may contain one or more shape-memory alloys, e.g., nitinol and/or spring-loaded steel.

Absorbable materials may be advantageous where there is a potential for misfiring or improper locating of the various implants. For example, in a situation where the driver drives an anchor 200, 1200 at an unintended location, or where the tissue does not properly receive the anchor 200, 1200, the anchor 200, 1200 even where not needed, would be relatively harmless, as it would eventually absorb into the patient's body.

Although particular example surgical applications have been described above, the devices 5, 1005 are in no way limited to these examples.

Although the present invention has been described with reference to particular examples and exemplary embodiments, it should be understood that the foregoing description is in no manner limiting. Moreover, the features described herein may be used in any combination.

What is claimed is:

1. A device, comprising:
    a plurality of anchors;
    at least one elastic closure element coupled to the anchors, configured to urge the anchors toward each other, and pre-tensioned against the configuration to urge the anchors toward each other; and
    a driver configured to drive the anchors, with the at least one elastic closure element coupled to the anchors, into tissue;
    wherein the at least one elastic closure element has an elasticity sufficient to urge the anchors, driven into the tissue, toward each other to close an aperture in the tissue located between the anchors driven into the tissue and to resist opposing forces exerted on the anchors that urge the anchors apart.

2. The device according to claim 1, wherein the opposing forces are exerted on the anchors by at least one of (a) the tissue, (b) a fluid flow, (c) pneumatic pressure, (d) hydraulic pressure, and (e) external forces.

3. The device according to claim 1, further comprising a safety release mechanism including a plurality of spring-loaded members, each spring-loaded member independently movable between an engagement position and a disengagement position, the safety release mechanism adapted to prevent the driver from driving the anchors unless all of the spring-loaded members are in the engagement position.

4. The device of claim 1, wherein the anchors each include an elongated body having a distal tip configured to pierce the tissue when the respective anchor is distally driven into the tissue.

5. The device of claim 4, wherein the anchors each include an anchoring projection configured to resist proximal movement of the anchor after the anchor is driven into the tissue.

6. The device of claim 5, wherein the anchoring projection is a wing extending proximally and radially from a connection between the wing and the elongated body to a free end.

7. The device of claim 6, wherein the wing includes a plurality of proximally extending cutting projections at the free end of the wing.

8. The device of claim 6, wherein the wing is formed by a cut progressing radially inwardly and distally into the elongated body.

9. The device of claim 8, wherein the elongated body and the wing include a plurality of longitudinally extending corrugations, the corrugations providing a plurality of proximally extending cutting projections at the free end of the wing.

10. The device of claim 4, the elongated body having a length extending between a proximal end and the distal tip, wherein the anchors each include first and second anchoring projections configured to resist proximal movement of the anchor after the anchor is driven into the tissue, each of the first and second anchoring projections being disposed at respective positions that are offset from other anchoring projections along the length of the elongated body.

11. The device of claim 10, wherein the first and second anchoring projections are first and second wings formed respectively by first and second cuts progressing radially inwardly and distally into the elongated body, each of the first and second cuts ending at respective locations that are offset from other cuts along the length of the elongated body.

12. The device of claim 1, wherein the at least one elastic closure element includes at least one of a band, an elastomeric band, and a band formed of silicon.

13. The device of claim 12, wherein the anchors each include a hooked projection configured to receive the band.

14. The device of claim 13, wherein the hooked projection is configured to maintain engagement between the band and the anchor by preventing the band from moving off the proximal end of the anchor.

15. The device of claim 1, wherein the device includes a plurality of closure elements.

16. The device of claim 15, wherein each of the plurality of closure elements contacts two or more of the anchors.

17. The device of claim 15, wherein the closure elements form a pattern of two overlapping V-shaped configurations.

18. The device of claim 15, wherein the plurality of closure elements contacts three or more of the anchors.

19. The device of claim 1, wherein the at least one closure element includes a monolithic V-shaped element coupling three of the anchors.

20. The device of claim 1, wherein the device includes two monolithic V-shaped closure elements each configured to contact three of the anchors.

21. The device of claim 20, wherein the two V-shaped closure elements overlap to form a diamond-shaped operational window.

22. The device of claim 1, further comprising a centering element configured to receive a guide wire.

23. The device of claim 22, wherein the centering element is a tubular shaft.

24. The device of claim 1, wherein the anchors are disposed along a ring-shaped circumference in a first configuration.

25. The device of claim 24, wherein the at least one closure element is prevented from extending within the ring-shaped circumference by one or more tubes.

26. The device of claim 1, wherein the driver is configured to simultaneously drive the plurality of anchors.

27. The device of claim 26, wherein the driver comprises a spring-loaded element configured to impact and impart a distally directed momentum to the anchors.

28. The device of claim 27, further comprising a trigger configured to release the spring-loaded element from a pre-loaded position in order to drive the plurality of anchors.

29. The device of claim 28, further comprising a handle, the trigger being disposed in the handle.

30. The device of claim 29, further comprising a cannula and an outer working tube, wherein the handle, the trigger, and the driver are detachable from the cannula, the outer working tube, the plurality of anchors, and the at least one elastic closure element.

31. The device of claim 1, wherein the plurality of anchors and the at least one closure element are formed of bioabsorbable materials.

32. The device of claim 1, further comprising
a cannula; and
an outer working tube;
wherein the at least one elastic closure element is pre-tensioned about the cannula and the outer working tube.

33. A device, comprising:
a plurality of anchors; and
at least one elastic closure element coupled to the anchors, configured to urge the anchors toward each other, and pre-tensioned against the configuration to urge the anchors toward each other;
wherein the at least one elastic closure element has an elasticity sufficient to urge the anchors, driven into tissue, toward each other to close an aperture in the tissue located between the anchors driven into the tissue and to resist opposing forces exerted on the anchors that urge the anchors apart.

34. The device according to claim 33, wherein the opposing forces are exerted on the anchors by at least one of (a) the tissue, (b) a fluid flow, (c) pneumatic pressure, (d) hydraulic pressure, and (e) external forces.

* * * * *